US012766210B2

(12) United States Patent
Shane et al.

(10) Patent No.: US 12,766,210 B2
(45) Date of Patent: Oct. 20, 2026

(54) METHOD AND SYSTEM FOR DECONTAMINATING SMALL ENCLOSURES

(71) Applicant: TOMI Environmental Solutions, Inc., Frederick, MD (US)

(72) Inventors: Halden Stuart Shane, Beverly Hills, CA (US); Johnny Sullivan Cato, Lynwood, CA (US)

(73) Assignee: TOMI Environmental Solutions, Inc., Frederick, MD (US)

( * ) Notice: Subject to any disclaimer, the term of this patent is extended or adjusted under 35 U.S.C. 154(b) by 1258 days.

(21) Appl. No.: 16/391,812

(22) Filed: Apr. 23, 2019

(65) Prior Publication Data

US 2019/0247529 A1 Aug. 15, 2019

Related U.S. Application Data

(63) Continuation-in-part of application No. 15/858,446, filed on Dec. 29, 2017, now Pat. No. 10,398,795.

(51) Int. Cl.
*A61L 2/22* (2006.01)

(52) U.S. Cl.
CPC ............. *A61L 2/22* (2013.01); *A61L 2202/14* (2013.01); *A61L 2202/15* (2013.01)

(58) Field of Classification Search
CPC ........... A61L 2/12; A61L 2/22; A61L 2202/14
See application file for complete search history.

(56) References Cited

U.S. PATENT DOCUMENTS 4,068,472 A * 1/1978 Takata ................ F02D 41/1441 477/181
5,217,165 A 6/1993 Takahashi et al.
5,902,552 A 5/1999 Brickley
6,656,424 B1 12/2003 Deal
6,706,243 B1 3/2004 Sias et al.
6,953,549 B2 10/2005 Hill et al.
7,354,551 B2 * 4/2008 Mielnik .................. A61L 2/208 422/32
2003/0035754 A1 2/2003 Sias et al.
2005/0224596 A1 * 10/2005 Panopoulos .......... A01M 25/00 239/722

(Continued)

FOREIGN PATENT DOCUMENTS

CN 103920176 7/2014
GB 2551544 * 12/2017

(Continued)

OTHER PUBLICATIONS

U.S. Appl. No. 15/858,446, filed Dec. 29, 2017, Pending.

(Continued)

*Primary Examiner* — Donald R Spamer
(74) *Attorney, Agent, or Firm* — John Murray

(57) ABSTRACT

A method, system and apparatus are described for decontaminating small enclosures, semi-enclosed and closed areas of pathogens by using a very dry mist comprising ionized hydrogen peroxide. The system can be controlled manually by the user, or by a remote connection, such as a wireless network connection. The method includes use of a handheld, (Continued)

point-and-spray device that sprays a very dry mist comprising ionized hydrogen peroxide under manual or automated control.

17 Claims, 12 Drawing Sheets

(56) References Cited

U.S. PATENT DOCUMENTS

| | | | | |
|---|---|---|---|---|
| 2007/0210186 | A1 | 9/2007 | Fenton et al. | |
| 2007/0224080 | A1 | 9/2007 | Sparks et al. | |
| 2007/0292305 | A1* | 12/2007 | Dempsey | A61L 2/206 422/33 |
| 2008/0219884 | A1* | 9/2008 | Berentsveig | A61L 2/24 422/33 |
| 2010/0178196 | A1 | 7/2010 | Garner | |
| 2011/0081273 | A1 | 4/2011 | Sunderland | |
| 2016/0158400 | A1* | 6/2016 | He | A61L 9/20 250/455.11 |
| 2016/0298857 | A1 | 10/2016 | Weng | |
| 2017/0312376 | A1* | 11/2017 | Bae | H05H 1/48 |
| 2017/0317623 | A1 | 11/2017 | Taniguchi et al. | |

FOREIGN PATENT DOCUMENTS

| | | |
|---|---|---|
| WO | 2014076013 | 5/2014 |
| WO | 2017004238 | 1/2017 |
| WO | PCT/US18/67843 | 12/2018 |

OTHER PUBLICATIONS

U.S. Appl. No. 16/391,812, filed Apr. 23, 2019, Pending.

Extended European Search Report of Application No. 18894052.2 mailed Mar. 28, 2022.

Paxton, H., "Use of Novel Approaches to Reduce Clostridium Difficile in an Inner City Hospital", Mar. 20, 2017, p. 4, InfectionControl.tips.

International Search Report and the Written Opinion of International application No. PCT/US2018/067843 mailed Mar. 25, 2019.

File History of U.S. Appl. No. 15/858,446, filed Dec. 29, 2017.

* cited by examiner

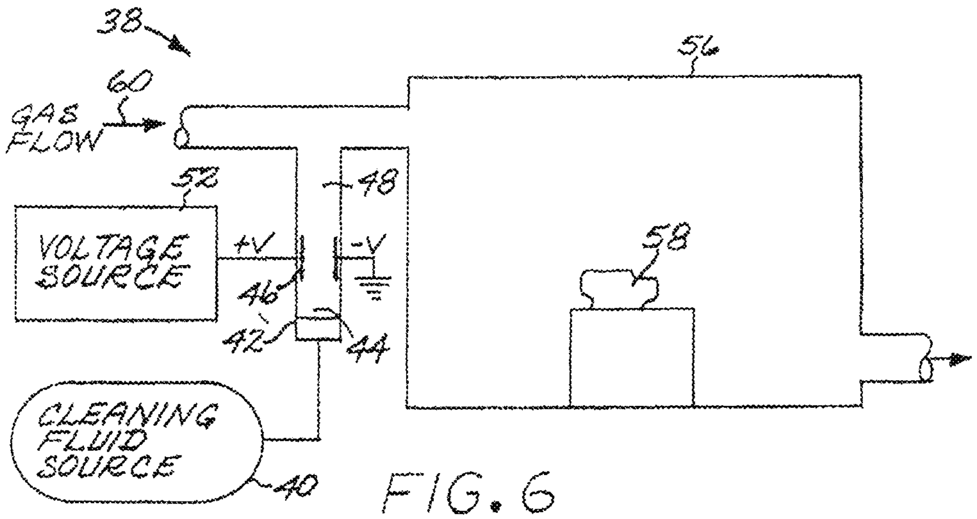
FIG. 6
FIG. 7
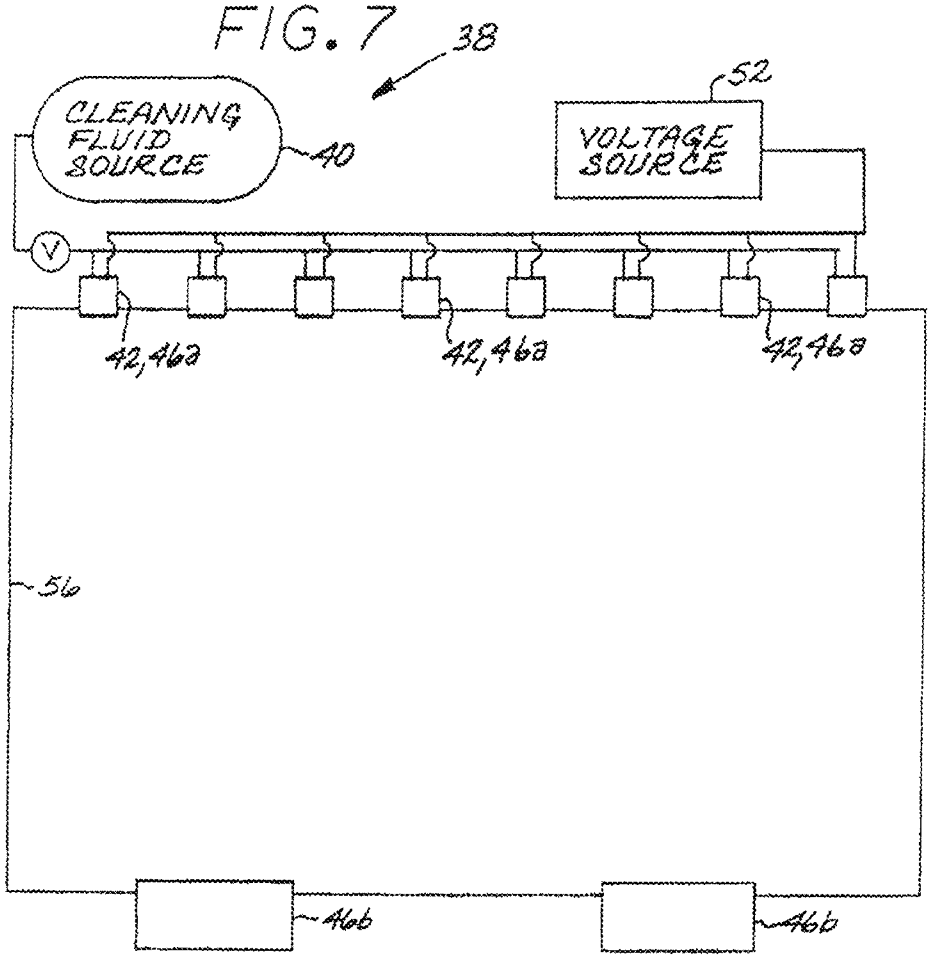

METHOD AND SYSTEM FOR DECONTAMINATING SMALL ENCLOSURES

This application is a continuation-in-part of U.S. application Ser. No. 15/858,446, filed on Dec. 29, 2017. The entirety of the aforementioned application is incorporated herein by reference.

FIELD

The present application relates generally to an apparatus and method for decontaminating articles, enclosed spaces, and unenclosed spaces and, more particularly, to microbiological decontamination of such locations.

BACKGROUND

Microbiological species are widely distributed in our environment. Most microbiological species are of little concern, because they do not damage other living organisms. However, other microbiological species may infect man or animals and cause them harm. The removing or rendering ineffective of injurious microbiological organisms has long been of interest. Drugs and medical devices are sterilized and packaged in sterile containers. Medical environments such as operating rooms, wards, and examination rooms are decontaminated by various cleaning procedures so that injurious microbiological organisms cannot spread from one patient to another.

Many available technologies for controlling microbiological organisms are of limited value in the public health circumstances of biological warfare and bioterrorism. However, current technologies addressing these instances are limited in their effectiveness in tightly enclosed environments.

One of the challenges of controlling microbiological organisms relates to decontaminating small enclosures. In such environments, it is not uncommon for a mist of decontaminants to travel on compressed air as far as several feet under normal settings. In a small enclosure, excessive reach of the sprayed mist results in several undesired outcomes. One such drawback is saturating surfaces in the vicinity of the mist applicators, or surfaces opposite to the applicators, for example. Moreover, improper mist regulation may result in wetter, denser fog, thereby affecting visibility and breathability in a small enclosure. Accordingly, the released mist undesirably increases moisture accumulation and condensation, the redressing of which requires increased aeration times.

A new approach is needed that is more readily usable in small enclosures with enhanced kill, and simpler maintenance of machinery. The present application fulfills this need, and further provides related advantages.

SUMMARY

An aspect of the application is directed to a method for decontaminating a small enclosure, comprising the steps of: entering input parameters of the small enclosure into a processing unit, wherein the processing unit is programmed to determine fluid properties of a cleaning fluid in a decontamination device based on the input parameters of the small enclosure, activating a decontamination cycle of the decontamination device, wherein the decontamination cycle comprises the steps of: providing a reservoir of the cleaning fluid; setting the determined fluid properties of the cleaning fluid; generating a very dry mist comprising ionized hydrogen peroxide of the cleaning fluid, wherein the generated very dry mist is applied to decontaminate the small enclosure.

In certain embodiments, the decontamination device is operated manually. In particular embodiments, the decontamination device is hand-held.

In certain embodiments, the input parameters of the small enclosure comprise: dimensions of the small enclosure, a position of the decontamination device relative to boundaries of the small enclosure, air temperature, pressure, and humidity of the small enclosure. In particular embodiments, the set fluid properties of the cleaning fluid comprise air pressure and fluid flow rate. In other embodiments, the setting of the determined fluid properties to the cleaning fluid is performed by controlling an air valve. In certain embodiments, the air valve is controlled by programming the processing unit to control a potentiometer. In various embodiments, the determined fluid properties of the cleaning fluid are adjusted by a size and a shape of a tube located at an exit of the cleaning fluid out of the decontamination device.

In particular embodiments, the fluid properties of the cleaning fluid are set by lowering the air pressure and the fluid flow rate respectively below a predetermined standard air pressure and a predetermined standard fluid flow rate.

In other embodiments, input parameters of a target area are entered into a processing unit, wherein the processing unit is further programmed to determine the fluid properties of the cleaning fluid in the decontamination device based on the input parameters of the target area. The input parameters of the small enclosure may be manually input. The input parameters of the small enclosure are measured by a plurality of sensors that are in networked communication with the processing unit.

In particular embodiments, the processing unit and the decontamination device are in wireless communication.

Another aspect of the application is a system for decontaminating a small enclosure, comprising a decontamination device and a computer processor, wherein the computer processor is in networked communication with the decontamination device, wherein input parameters of the small enclosure are entered into the computer processor, wherein the computer processor is programmed to determine fluid properties of a cleaning fluid in the decontamination device based on the input parameters of the small enclosure, wherein the computer processor is further programmed to activate a decontamination cycle of the decontamination device, the decontamination cycle comprising the steps of: providing a reservoir of the cleaning fluid; setting the determined fluid properties of the cleaning fluid; generating a very dry mist of the cleaning fluid, wherein the generated very dry mist is applied to decontaminate the small enclosure.

These and other aspects and embodiments of the present application will become better understood with reference to the following detailed description when considered in association with the accompanying drawings and claims.

BRIEF DESCRIPTION OF THE DRAWINGS

FIG. 6 illustrates a chamber-based decontamination apparatus.

FIG. 7 illustrates a decontamination apparatus for decontaminating a room.

Figure 1:
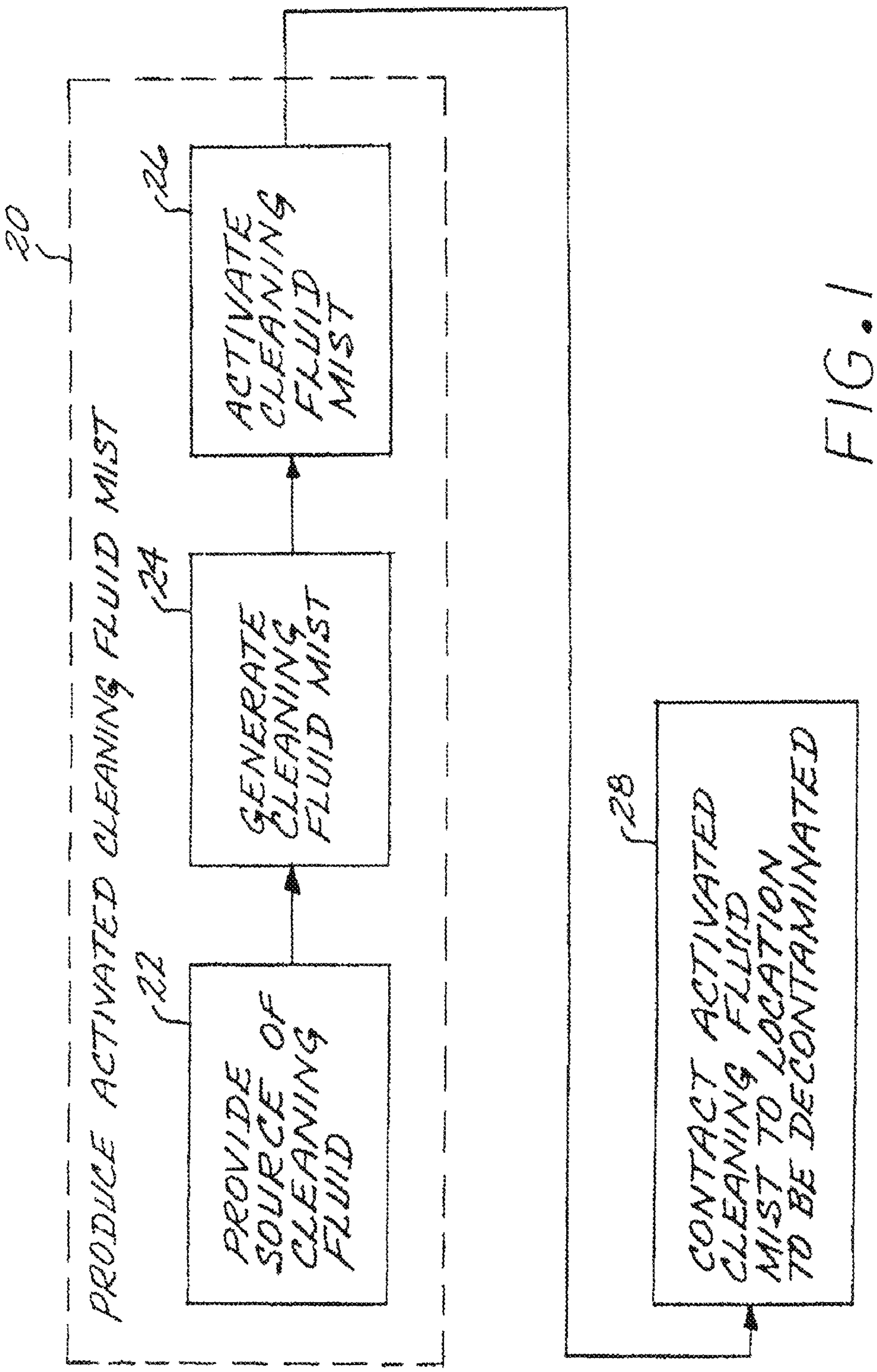
FIG. 1 is a block flow diagram of a general approach for denaturing a biochemical agent using an activated cleaning fluid mist.

Throughout the drawings, the same reference numerals and characters, unless otherwise stated are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and appended claims.

DETAILED DESCRIPTION

Reference will be made in detail to certain aspects and exemplary embodiments of the application, illustrating examples in the accompanying structures and figures. The aspects of the application are described in conjunction with the exemplary embodiments, including methods, materials and examples, such description is non-limiting and the scope of the application is intended to encompass all equivalents, alternatives, and modifications, either generally known, or incorporated here. With respect to the teachings in the present application, any issued patent, pending patent application or patent application publication described in this application is expressly incorporated by reference herein.

Unless defined otherwise, all technical and scientific terms used herein have the same meanings as commonly understood by one of skill in the art to which the disclosed method and compositions belong. It must be noted that as used herein and in the appended claims, the singular forms "a," "an," and "the" include plural reference unless the context clearly dictates otherwise. Thus, for example, reference to "a peptide" includes "one or more" peptides or a "plurality" of such peptides.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to "the value," greater than or equal to the value" and possible ranges between values are also disclosed, as appropriately understood by the skilled artisan. For example, if the value "10" is disclosed the "less than or equal to 10" as well as "greater than or equal to 10" is also disclosed.

As used herein, the term "ultrasonic cavitation" means the use of ultrasonic sound to cavitate a fluid, such as a cleaning fluid. Ultrasonic cavitation can be applied to a fluid by a range of methods and devices known to one of skill in the art, including a high pressure ultrasonic nebulizer, an ultrasonic nozzle, or an ultrasonic wafer. As used herein, the term "ultrasonic" means frequencies of sound above the audible range, including anything over 20 kHz.

As used herein, the term "ultrasonic cavitator" means a device used to perform ultrasonic cavitation on a cleaning fluid. Examples of an ultrasonic cavitator include a high pressure ultrasonic nebulizer, an ultrasonic nozzle, or an ultrasonic wafer. For example, a high pressure ultrasonic nebulizer atomizes liquid particles at a pressure of 50 to 400 bar to produce aerosol droplets. An ultrasonic nozzle is a spray nozzle that uses high frequency vibration produced by piezoelectric transducers to cavitate a liquid. A preferred embodiment uses an ultrasonic wafer. In one embodiment the ultrasonic wafer is a ceramic diaphragm vibrating at an ultrasonic frequency to create water droplets. In another embodiment, the ultrasonic wafer is a small metal plate that vibrates at high frequency to cavitate a liquid. One of ordinary skill will understand that the choice of ultrasonic cavitator is not limiting on the scope of this application.

As used herein, the term "decontaminating" means acting to neutralize or remove pathogens from an area or article. As used herein, the term "pathogen" includes, but is not limited to, a bacterium, yeast, protozoan, virus, or other pathogenic microorganisms. The term "pathogen" also encompasses targeted bioterror agents.

As used herein, the term "bacteria" shall mean members of a large group of unicellular microorganisms that have cell walls but lack organelles and an organized nucleus. Synonyms for bacteria may include the terms "microorganisms", "microbes", "germs", "bacilli", and "prokaryotes." Exemplary bacteria include, but are not limited to *Mycobacterium* species, including *M. tuberculosis; Staphylococcus* species, including *S. epidermidis, S. aureus*, and methicillin-resistant *S. aureus; Streptococcus* species, including *S. pneumoniae, S. pyogenes, S. mutans, S. agalactiae, S. equi, S. canis, S. bovis, S. equinus, S. anginosus, S. sanguis, S. salivarius, S. mitis*; other pathogenic Streptococcal species, including *Enterococcus* species, such as *E. faecalis* and *E. faecium; Haemophilus influenzae, Pseudomonas* species, including *P. aeruginosa, P. pseudomallei*, and *P. mallei; Salmonella* species, including *S. enterocolitis, S. typhimurium, S. enteritidis, S. bongori*, and *S. choleraesuis; Shigella* species, including *S. flexneri, S. sonnei, S. dysenteriae*, and *S. boydii; Brucella* species, including *B. melitensis, B. suis, B. abortus*, and *B. pertussis; Neisseria* species, including *N. meningitidis* and *N. gonorrhoeae; Escherichia coli*, including enterotoxigenic *E. coli* (ETEC); *Vibrio cholerae, Helicobacter pylori, Geobacillus stearothermophilus, Chlamydia trachomatis, Clostridium difficile, Cryptococcus neoformans, Moraxella* species, including *M. catarrhalis, Campylobacter* species, including *C. jejuni; Corynebacterium* species, including *C. diphtheriae, C. ulcerans, C. pseudotuberculosis, C. pseudodiphtheriticum, C. urealyticum, C. hemolyticum, C. equi; Listeria monocytogenes, Nocardia asteroides, Bacteroides* species, *Actinomycetes* species, *Treponema pallidum, Leptospirosa species, Klebsiella pneumoniae; Proteus* sp., including *Proteus vulgaris; Serratia* species, *Acinetobacter, Yersinia* species, including *Y. pestis* and *Y. pseudotuberculosis; Francisella tularensis, Enterobacter species, Bacteroides species, Legionella species, Borrelia burgdorferi*, and the like. As used herein, the term "targeted bioterror agents" includes, but is not limited to, anthrax (*Bacillus antracis*), plague (*Yersinia pestis*), and tularemia (*Franciscella tularensis*).

As used herein, the term "virus" can include, but is not limited to, influenza viruses, herpesviruses, polioviruses, noroviruses, and retroviruses. Examples of viruses include, but are not limited to, human immunodeficiency virus type 1 and type 2 (HIV-1 and HIV-2), human T-cell lymphotropic virus type I and type II (HTLV-I and HTLV-II), hepatitis A virus, hepatitis B virus (HBV), hepatitis C virus (HCV), hepatitis delta virus (HDV), hepatitis E virus (HEV), hepatitis G virus (HGV), parvovirus B19 virus, hepatitis A virus, hepatitis G virus, hepatitis E virus, transfusion transmitted virus (TTV), Epstein-Barr virus, human cytomegalovirus type 1 (HCMV-1), human herpesvirus type 6 (HHV-6), human herpesvirus type 7 (HHV-7), human herpesvirus type 8 (HHV-8), influenza type A viruses, including subtypes H1N1 and H5N1, human metapneumovirus, severe acute respiratory syndrome (SARS) coronavirus, hantavirus, and RNA viruses from Arenaviridae (e.g., Lassa fever virus (LFV)), Pneumoviridae (e.g., human metapneumovirus), Filoviridae (e.g., Ebola virus (EBOV), Marburg virus (MBGV) and Zika virus); Bunyaviridae (e.g., Rift Valley fever virus (RVFV), Crimean-Congo hemorrhagic fever virus (CCHFV), and hantavirus); Flaviviridae (West Nile virus (WNV), Dengue fever virus (DENV), yellow fever virus (YFV), GB virus C (GBV-C; formerly known as hepatitis G virus (HGV)); Rotaviridae (e.g., rotavirus), and combinations thereof. In one embodiment, the subject is infected with HIV-1 or HIV-2.

As used herein, the term "fungi" shall mean any member of the group of saprophytic and parasitic spore-producing eukaryotic typically filamentous organisms formerly classified as plants that lack chlorophyll and include molds, rusts, mildews, smuts, mushrooms, and yeasts. Exemplary fungi include, but are not limited to, *Aspergillus* species, *Dermatophytes, Blastomyces dermatitidis, Candida* species, including *C. auris, C. albicans* and *C. krusei; Malassezia furfur, Exophiala werneckii, Piedraia hortai, Trichosporon beigelii, Pseudallescheria boydii, Madurella grisea, Histoplasma capsulatum, Sporothrix schenckii, Histoplasma capsulatum, Tinea* species, including *T. versicolor, T. pedis T. unguium, T. cruris, T. capitus, T. corporis, T. barbae; Trichophyton* species, including *T. rubrum, T. interdigitale, T. tonsurans, T. violaceum, T. yaoundei, T. schoenleinii, T. megninii, T. soudanense, T. equinum, T. erinacei*, and *T. verrucosum; Mycoplasma genitalia; Microsporum* species, including *M. audouini, M. ferrugineum, M. canis, M. nanum, M. distortum, M. gypseum, M. fulvum*, and the like.

As used herein, the term "protozoan" shall mean any member of a diverse group of eukaryotes that are primarily unicellular, existing singly or aggregating into colonies, are usually nonphotosynthetic, and are often classified further into phyla according to their capacity for and means of motility, as by pseudopods, flagella, or cilia. Exemplary protozoans include, but are not limited to *Plasmodium* species, including *P. falciparum, P. vivax, P. ovale*, and *P. malariae; Leishmania* species, including *L. major, L. tropica, L. donovani, L. infantum, L. chagasi, L. mexicana, L. panamensis, L. braziliensis* and *L. guyanensi; Cryptosporidium, Isospora belli, Toxoplasma gondii, Trichomonas vaginalis*, and *Cyclospora* species.

As used herein, the term "article" means any solid item or object that may be susceptible to contamination with pathogens. As used herein, the term "substantially enclosed space" means a room, a tent, a building, or any man-made structure that is substantially enclosed and may be susceptible to contamination with pathogens. The term "substantially enclosed space" is not limited to man-made structures, even though embodiments illustrated herein may be preferably directed to decontamination of such structures As used herein, the term "sensor" can refer to any type of sensor suitable for detecting contamination on an apparatus, a surface, or in a substantially closed space. Examples of sensors include, but are not limited to, photosensors, voltaic sensors, weight sensors, moisture sensors, pressure sensors, or any type of biosensor.

As used herein, the term "shearing" refers to the process of using force to fragment liquid particles into discrete groups that move and flow as energized independent subgroups of sheared particles until the groups of particles transition in fluid phase into a mist. As used herein, the term "mist" means a cloud of aerosol droplets. As used herein, the term "aerosol" is a colloid of fine liquid droplets of about 1 to about 20 micrometers in diameter.

As used herein, the term "cleaning fluid" refers to the source of an active species used to decontaminate an article or substantially enclosed space. The preferred active species is hydroxyl ions, and the preferred source is hydrogen peroxide. The source may instead be a more-complex species that produces hydroxyl ions upon reaction or decomposition. Examples of such more-complex species include peracetic acid ($CH_2COO—OH+H_2O$), sodium percarbonate ($2Na_2CO_3+3H_2O_2$), and gluteraldehyde ($CH_8O_2$). The cleaning fluid may further include promoting species that aid the active species in accomplishing its attack upon the biological microorganisms. Examples of such promoting species include ethylenediaminetetraacetate, isopropyl alcohol, enzymes, fatty acids, and acids. The cleaning fluid is of any operable type. The cleaning fluid must contain an activatable species. A preferred cleaning fluid comprises a source of hydroxyl ions ($OH^-$) for subsequent activation. Such a source may be hydrogen peroxide ($H_2O_2$) or a precursor species that produces hydroxyl ions. Other sources of hydroxyl ions may be used as appropriate. Examples of other operable sources of hydroxyl ions include peracetic acid ($CH_2COO—OH+H_2O$), sodium percarbonate ($2Na_2CO_3+3H_2O_2$), and gluteraldehyde ($CH_8O_2$). Other activatable species and sources of such other activatable species may also be used. In some embodiments, activated ionic particles are generated by passing Water for Injection (WFI) through the arc, providing greater than $3\text{-log}^{10}$ killing of bacteria, bacterial spores, or virus particles relative to untreated controls.

The cleaning fluid may also contain promoting species that are not themselves sources of activatable species such as hydroxyl ions, but instead modify the decontamination reactions in some beneficial fashion. Examples include ethylenediaminetetraacetate (EDTA), which binds metal ions and allows the activated species to destroy the cell walls more readily; an alcohol such as isopropyl alcohol, which improves wetting of the mist to the cells; enzymes, which speed up or intensity the redox reaction in which the activated species attacks the cell walls; fatty acids, which act as an ancillary anti-microbial and may combine with free radicals to create residual anti-microbial activity; and acids such as citric acid, lactic acid, or oxalic acid, which speed up or intensity the redox reaction and may act as ancillary anti-microbial species to pH-sensitive organisms. Mixtures of the various activatable species and the various promoting species may be used as well. The cleaning fluids are preferably aqueous solutions, but may be solutions in organics such as alcohol. The cleaning fluid source may be a source of the cleaning fluid itself, or a source of a cleaning fluid precursor that chemically reacts or decomposes to produce the cleaning fluid.

As used herein, the term "a nonthermal plasma actuator" means an actuator that activates the cleaning fluid to an activated condition such as the ionized, plasma, or free radical states which, with the passage of time, returns to the non-activated state (a process termed "recombination"). To accomplish the activation, the activator produces activating energy such as electric energy or photonic energy. The photonic energy may be produced by a laser. Examples of activators include an AC electric field, an AC arc, a DC electric field, a DC arc, an electron beam, an ion beam, a microwave beam, a radio frequency beam, and an ultraviolet light beam. The activator may include a tuner that tunes the amplitude, frequency, wave form, or other characteristic of the activating energy to achieve a desired, usually a maximum, re-combination time of the activated cleaning fluid mist. As used herein, the term "plasma activated ionic particles" means activated $OH^-$ ions.

As used herein, an "enclosed space" refers to any chamber, container or space that can be decontaminated with the system of the present disclosure. Examples of enclosed spaces include, but are not limited to, any chamber used in everyday to highly controlled research projects/spaces, sanitation chambers (such as gynoprobe cabinets), BSC, glovebox, research hoods and clinical spaces.

A System for Decontaminating a Substantially Enclosed Space of an Airborne Pathogen An aspect of the application is a system for decontaminating a substantially enclosed space, comprising: a sensor for airborne pathogens, wherein the sensor is in networked communication with a computer processor; a computer processor, wherein the computer processor is in networked communication with the sensor and a decontamination apparatus; a decontamination apparatus, wherein the decontamination apparatus is in networked communication with the computer processor, and further wherein the decontamination apparatus comprises: a reservoir of cleaning fluid; an ultrasonic cavitator, wherein the ultrasonic cavitator is submerged in the reservoir; a nonthermal plasma actuator, wherein the actuator activates a mist generated from the reservoir; a funnel, wherein the funnel connects the nonthermal plasma activator to the reservoir; an outer tube, wherein the outer tube connects the nonthermal actuator to the external atmosphere; and wherein a mist generated from the reservoir can pass through the funnel to the actuator, and further wherein after the mist is activated by the actuator the mist can pass through the outer tube to the external atmosphere.

In an exemplary embodiment, the computer system includes a memory, a processor, and, optionally, a secondary storage device. In some embodiments, the computer system includes a plurality of processors and is configured as a plurality of, e.g., bladed servers, or other known server configurations. In particular embodiments, the computer system also includes an input device, a display device, and an output device. In some embodiments, the memory includes RAM or similar types of memory. In particular embodiments, the memory stores one or more applications for execution by the processor. In some embodiments, the secondary storage device includes a hard disk drive, CD-ROM or DVD drive, or other types of non-volatile data storage. In particular embodiments, the processor executes the application(s) that are stored in the memory or the secondary storage, or received from the internet or other network. In some embodiments, processing by the processor may be implemented in software, such as software modules, for execution by computers or other machines. These applications preferably include instructions executable to perform the functions and methods described above and illustrated in the Figures herein. The applications preferably provide GUIs through which users may view and interact with the application(s). In other embodiments, the system comprises remote access to control and/or view the system.

In further embodiments, a decontamination system can interface with a building HVAC system for room isolation and aeration. The decontamination system uses automated equipment for decontamination of any closed area with downloadable disinfection/decontamination run data and real-time measurement of injection rates to ensure targeted injection volume. The decontamination system can encompass multiple rooms and customized specifications as required according to room size and usage. In another embodiment, the decontamination system is contained in a handheld device for use in a life science facility. The device is designed to be used by technicians using a trigger on the device to control its use according to the trigger position.

Method and Apparatus for Decontamination Using an Activated Cleaning Fluid Mist

As disclosed in U.S. Pat. No. 6,969,487, which is incorporated herein by reference, a method for performing decontamination comprises the steps of producing an activated cleaning fluid mist wherein at least a portion of the cleaning fluid mist is in an activated state, and contacting the activated cleaning fluid mist to a location to be decontaminated.

FIG. 1 depicts a preferred method for performing decontamination. An activated cleaning fluid mist is produced, numeral 20. Any operable approach may be used, and a preferred approach is illustrated within step 20 of FIG. 1. A source of a cleaning fluid is provided, numeral 22. The cleaning fluid is preferably a liquid that may be vaporized, by any means of force or energy, in ambient-pressure air to form a mist. The liquid cleaning fluid may be stored at one atmosphere or slightly greater pressure, while a cleaning fluid in a gaseous state usually requires pressurized storage. The source of the cleaning fluid may also be a precursor of the cleaning fluid, such as a solid, liquid, or gas that reacts, decomposes, or otherwise produces the cleaning fluid.

A cleaning fluid mist, containing the activatable species and the promoting species, if any, is generated, numeral 24. The mist generator to generate the cleaning fluid mist may be of any operable type. In the preferred case, the cleaning mist or vapor is fine droplets of the vaporized cleaning fluid. In some embodiments, the droplets are preferably roughly uniformly sized, on the order of from about 1 to about 20 micrometers in diameter. In other embodiments, the droplets are preferably roughly uniformly sized, on the order of from about 1 to about 10 micrometers in diameter. In still other embodiments, the droplets are preferably roughly uniformly sized, on the order of from about 1 to about 5 micrometers in diameter. In yet other embodiments, the droplets are preferably roughly uniformly sized, on the order of from about 2 to about 4 micrometers in diameter. Various types of mist generators have been used in prototype studies.

The cleaning fluid mist is activated to produce an activated cleaning fluid mist, numeral 26. The activation produces activated species of the cleaning fluid material in the mist, such as the cleaning fluid material in the ionized, plasma, or free radical states. At least a portion of the activatable species is activated, and in some cases some of the promoting species, if any, is activated. A high yield of activated species is desired to improve the efficiency of the decontamination process, but it is not necessary that all or even a majority of the activatable species achieve the activated state. Any operable activator may be used. The activator field or beam may be electrical or photonic. Examples include an AC electric field, an AC arc, a DC electric field, a DC arc, an electron beam, an ion beam, a microwave beam, a radio frequency beam, and an ultraviolet light beam produced by a laser or other source. The activator causes at least some of the activatable species of the cleaning fluid in the cleaning fluid mist to be excited to the ion, plasma, or free radical state, thereby achieving "activation." These activated species enter redox reactions with the cell walls of the microbiological organisms, thereby destroying the cells or at least preventing their multiplication and growth. In the case of the preferred hydrogen peroxide, at least some of the $H_2O_2$ molecules dissociate to produce hydroxyl ($OH^-$) and monatomic oxygen ($O^-$) ionic activated species. These activated species remain dissociated for a period of time, typically several seconds or longer, during which they attack and destroy the biological microorganisms. The activator is preferably tunable as to the frequency, waveform, amplitude, or other properties of the activation field or beam, so that it may be optimized for achieving a maximum recombination time for action against the biological microorganisms. In the case of hydrogen peroxide, the dissociated activated species recombine to form diatomic oxygen and water, harmless molecules.

Figure 2:
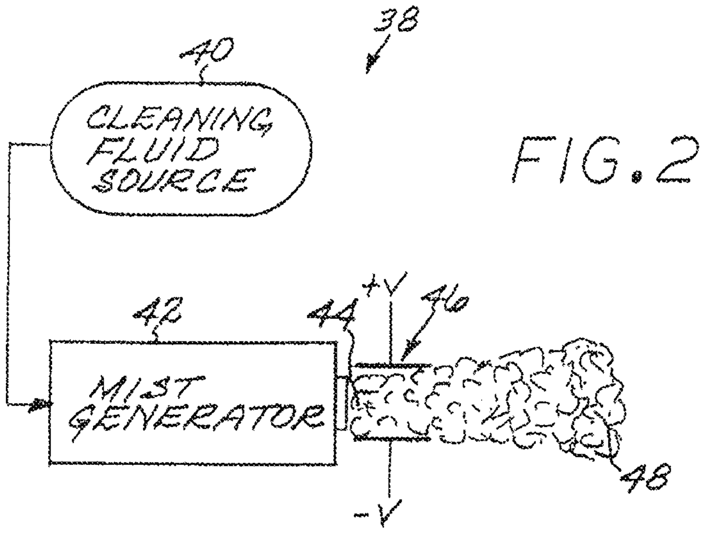
FIG. 2 is a schematic view of a first embodiment of apparatus for denaturing biological agents, with the activator proximally located to the mist generator.
Figure 3:
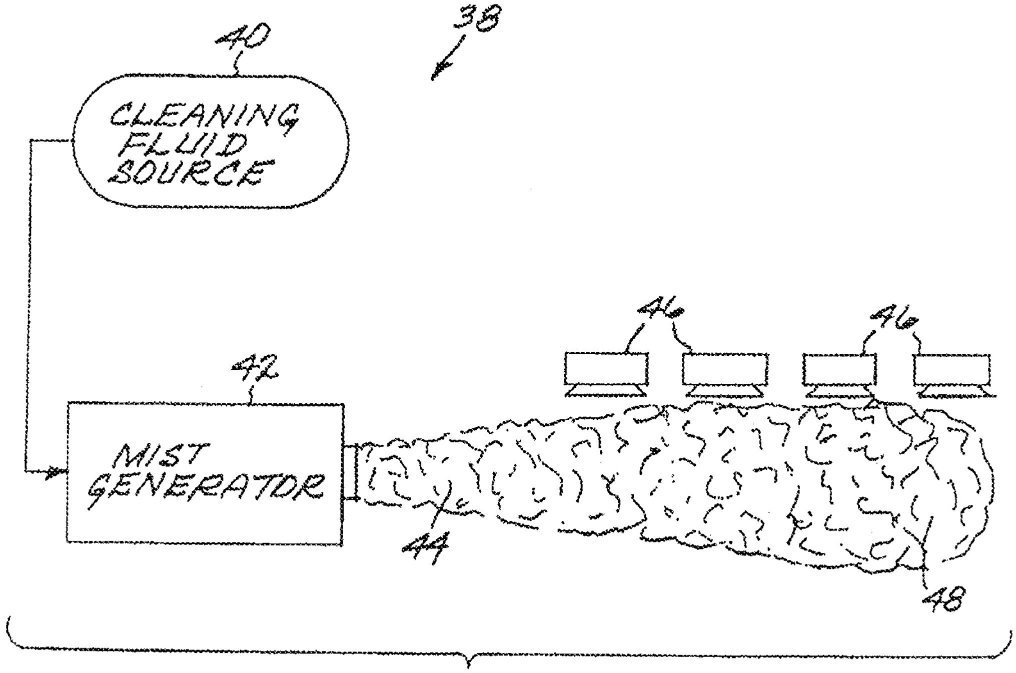
FIG. 3 is a schematic view of a second embodiment of apparatus for denaturing biological agents, with the activator located remotely from the mist generator.
Figure 4:
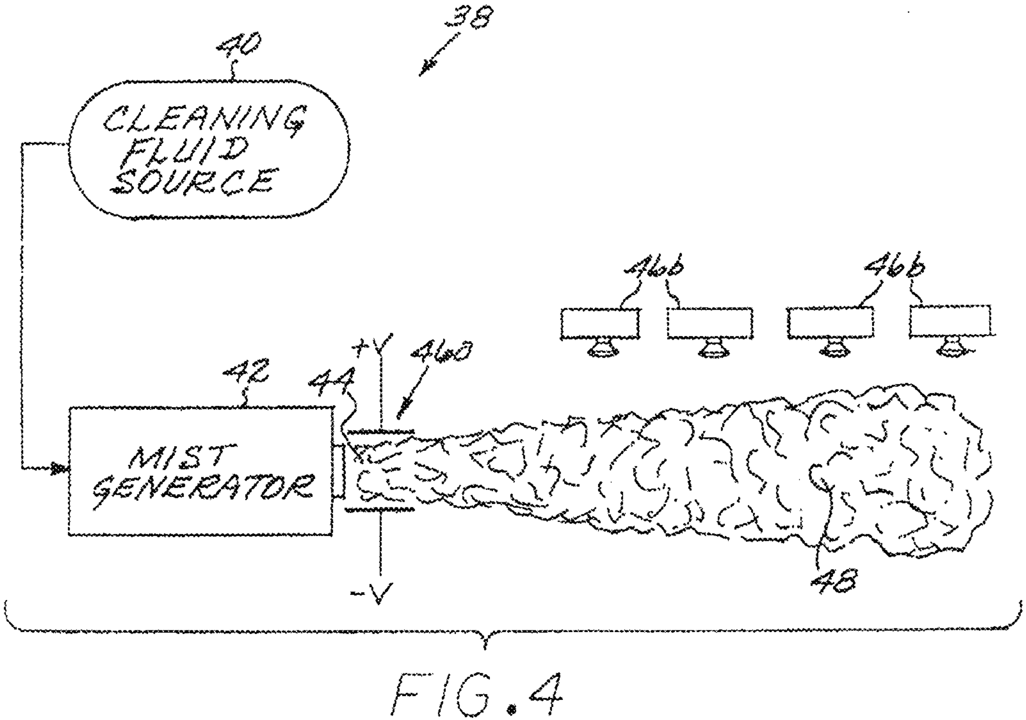
FIG. 4 is a schematic view of a third embodiment of apparatus for denaturing biological agents, with both proximate and remote activators.

The physical relationship of the mist generator and the activator may be of several types, illustrated schematically for three types of decontamination apparatus 38 in FIGS. 2-4. A source of the cleaning fluid 40 provides a flow of the cleaning fluid to a mist generator 42 in each case. The mist generator forms a cleaning fluid mist 44 of the cleaning fluid. The cleaning fluid mist 44 includes the activatable species and the promoting species, if any. In the embodiment of FIG. 2, an activator 46, schematically illustrated as a pair of electrical discharge plates between which the cleaning fluid mist 44 passes, is located proximate to, and preferably immediately adjacent to, the mist generator 42. The mist generator 42 and the activator 46 are typically packaged together for convenience in a single housing in this case. The cleaning fluid mist 44 leaving the mist generator 42 is immediately activated by the activator 46 to produce an activated cleaning fluid mist 48. In the embodiment of FIG. 3, the activator 46, here schematically illustrated as a set of microwave sources, is located remotely from the mist generator 42. The cleaning fluid mist 44 flows from mist generator 42 and remains as a non-activated cleaning fluid mist for a period of time, prior to passing into a region where it is in the influence of and activated by the activator 46. These two embodiments may be combined as shown in FIG. 4, where the cleaning fluid mist 44 is initially activated to form the activated cleaning fluid mist 48 by an activator **46*a* that is proximate to the mist generator 42, and then kept in the activated state or re-activated as necessary by an activator 46*b* that is remote from the mist generator 42. In this case, the activator 46*b* is illustrated to be an ultraviolet light source. The apparatus of FIG. 4 has the advantage that the cleaning fluid is initially activated and then maintained in an activated state for an extended period of time to achieve a prolonged effective state. These various types of apparatus 38** are used in differing situations according to the physical constraints of each situation, and some illustrative situations are discussed subsequently. Particle and/or gas filters may be provided where appropriate to remove particulate matter that is the carrier for microbiological organisms, and also to remove the residual cleaning mist and its reaction products.

The activated cleaning fluid mist 48 is contacted to locations that are to be decontaminated, numeral 28. The types of locations and the manner of contacting lead to a number of specific embodiments of the previously described general approaches, as described next.

Figure 5:
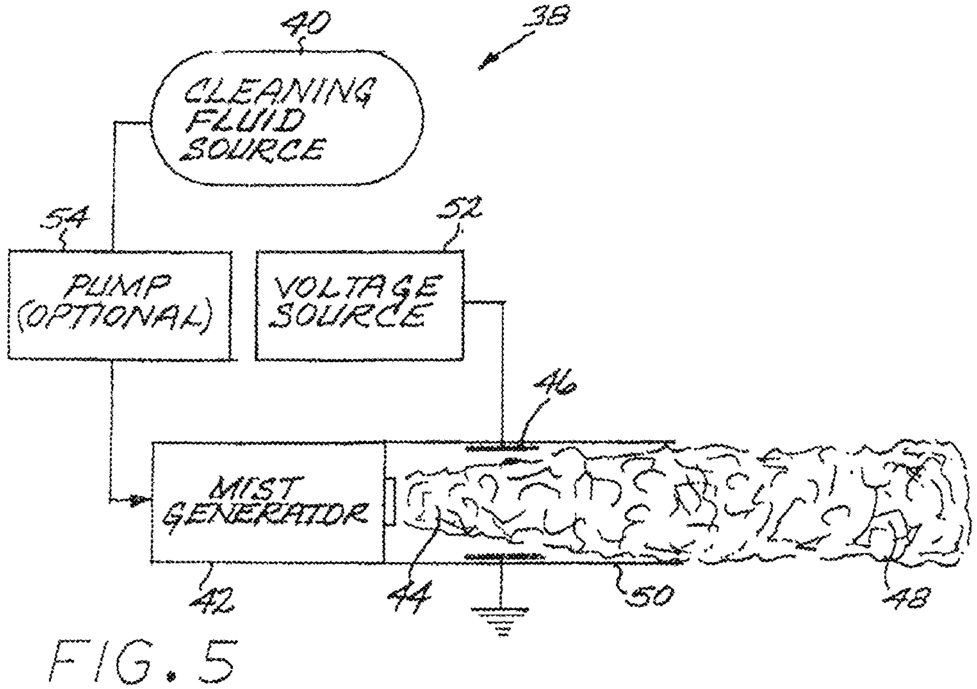
FIG. 5 illustrates a streaming decontamination apparatus.

FIG. 5 illustrates a streaming form of decontamination apparatus 38. This type of apparatus normally uses the general configuration shown in FIG. 2, where the activator 46 is located proximally to the mist generator 42. It does not require an enclosure, although it may be used within an enclosure. In FIG. 5 and other figures illustrating specific embodiments of the apparatus, the common elements of structure will be given the same reference numerals as used elsewhere, and the other description is incorporated into the description of each embodiment. Cleaning fluid from the cleaning fluid source 40 is supplied to the mist generator 42, and the cleaning fluid mist 44 flows from the mist generator 42. The cleaning fluid mist 44 flows through an interior of a tube 50 that channels and directs the flow of the cleaning fluid mist 44. The activator 46 powered by a voltage source 52 activates the cleaning fluid mist 44 as it flows through the interior of the tube 50, so that the activated cleaning fluid mist 48 flows from the tube 50 as a stream. The stream is directed into a volume or against an object that is to be decontaminated.

In one embodiment, the voltage source 52 is connected to an adjustable voltage divider, such as a potentiometer, for example. The potentiometer may include a housing that contains a resistive element and a contact that slides along the resistive element, two electrical terminals at the two ends of the resistive element, and a mechanism that moves the sliding contact from one end to the other. The potentiometer used may be a circular slider potentiometer, a liner slider potentiometer, or any other suitable slider arrangement may be used. The potentiometer may include a resistive element made of graphite, plastic containing carbon particles, resistance wire, or a mixture of ceramic and metal, for example.

The included potentiometer may allow a user to control the fluid flow rate of the cleaning fluid mist 44 flowing through the tube 50. As a result, the reduced air pressure may reduce the size of the produced mist/fog particle. This potentiometer may be controlled by a control unit in order to regulate input for the electric circuit of the voltage source 52.

This basic configuration of FIG. 5 may be scaled over a wide range of sizes. In one example, the cleaning fluid source 40 is a hand-held pressure can of the type commonly used to dispense fluids or gases. In another example, the cleaning fluid source 40 operates on two platforms, for example. One platform may be a handheld, point-and-spray surface decontamination device, and the other platform may be a programmable, automated environment decontamination device designed for small enclosures. The handheld, point-and-spray feature allows for manual control of the decontamination action. The programmable automation allows input of the surrounding parameters in order to predictably and consistently operate in an optimal arrangement with the geometry of the decontaminate enclosure.

The voltage source 52 is a battery and a circuit to supply a high voltage to the activation source 46 for a sufficient period to activate the amount of cleaning fluid that is stored within the pressure can. The tube 50 is the nozzle of the pressure can. In another example, the tube 50 is a hand-held wand operating from a larger-volume cleaning fluid source 40 and with a plug-in or battery electrical voltage source 52. The cleaning fluid source 40 may be pressurized to drive the flow of the cleaning fluid through the tube 50, or there may be provided an optional pump 54 that forces the cleaning fluid through the mist generator 42 and out of the tube 50 with great force.

In a programmable device, the control unit may be programmed to send instruction to adjust the potentiometer and control the pump 54 based on the desired fluid parameters. For example, in particularly small enclosures, a drier mist may be generated, in order for the mist to travel a shorter distance. This may be accomplished by reducing the standard air pressure, or the standard fluid flow rate of the decontamination device. The standard air pressure entered into the programmable control unit may be in the range between 25-50 psi, and the input standard air pressure range may be modified as deemed suitable. In addition, the standard fluid flow rate entered into the programmable control unit may be in the range between 25-50 ml/minute, and the input standard fluid flow rate range may be modified as considered appropriate.

In comparison with the programmable device, a handheld surface decontamination device may be manually operated by pressing the trigger on a handheld applicator to produce the decontamination fluid, such as ionized hydrogen peroxide mist. In one example, fluid or air settings are not programmably modified, but are, instead, manually controlled by the user based on the actual confines of the enclosure.

Other forms of the apparatus 38 are primarily used in conjunction with an enclosure, either to enclose the decontamination processing or an object or flow, or to achieve decontamination of the interior of the enclosure. FIG. 6 illustrates the apparatus 38 including an enclosure 56 that serves as a chamber in which an object 58 is decontaminated. The object 58 may be stationary, or it may move through the enclosure 56 on a conveyer. This embodiment also illustrates the form of the present apparatus wherein the activated cleaning fluid mist 48 is added to and mixed with another gas flow 60. The activated cleaning fluid mist 48 mixes with the gas flow 60, and the mixed gas flow contacts the object 58. This embodiment may be implemented either as a continuous-flow system, as illustrated, or as a batch system wherein the enclosure 56 is filled with the activated cleaning fluid mist 48 or with the mixture of the activated cleaning fluid mist 48 and the gas 60 in a batch-wise fashion.

In the embodiment of FIG. 7, the enclosure 56 is formed by the walls, floor, and ceiling of a room or other structure such as a vehicle. The activated cleaning fluid mist is produced by an integrated apparatus of the type illustrated in FIG. 4, in which the mist generator 42 and the activator **46*a* are packaged together as a single unit. An optional second activator 46*b* is provided and used in the manner described in relation to FIG. 4, whose disclosure is incorporated here. The second activator 46*b* maintains the activated cleaning fluid mist in the activated state for extended periods of time, so as to allow complete decontamination of the room. The second activator 46*b* may be built into the walls, floor, or ceiling of the enclosure 56, or they may be provided as portable units that are positioned within the enclosure 56 only during the decontamination processing. The decontamination apparatus 38 of FIG. 7 decontaminates the interior walls of the room, vehicle, or other structure, as well as objects and people therein. An apparatus 38 of the type shown in FIG. 7 may be used to decontaminate a room (or rooms) in a stationary home, office, or other facility, or the interior of a movable vehicle such as an aircraft, automobile, ship, or military vehicle. The enclosure 56** may also be a protective suit worn by decontamination personnel, to provide continuing decontamination of its interior for normal operation or in the event of a leak in the protective suit.

Figure 8:
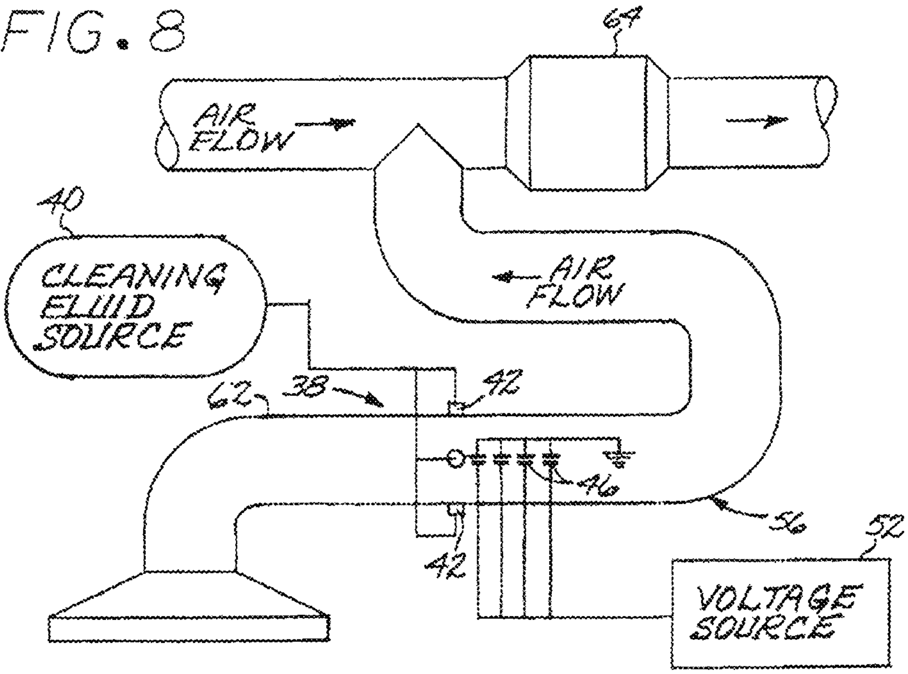
FIG. 8 illustrates a decontamination apparatus for a heating, ventilating, and air conditioning duct system.

FIG. 8 illustrates an embodiment wherein the mist generator 42 and the activator 46 are built into, or temporarily inserted into, an enclosure 56 in the form of a duct of the HVAC system. The duct 62 may be part of the main duct of the HVAC system, or it may be an auxiliary duct added to the HVAC system for receiving the decontamination apparatus 38. A filter 64 is provided downstream of the mist generator 42 and activator 46 for removing particulate and any remaining mist. The filter 64 may be, for example, a porous carbon, low-restriction coalescing filter of the known type.

Figure 9:
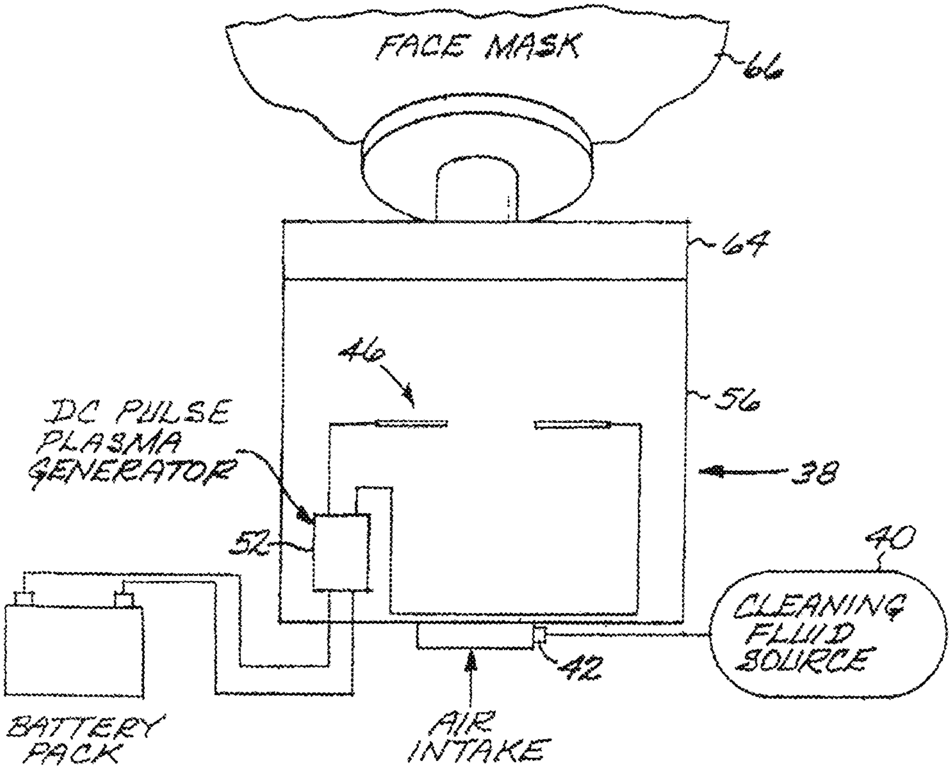
FIG. 9 illustrates a decontamination apparatus for air breathed by a person.

As illustrated by the embodiment of FIG. 8, the decontamination apparatus 38 may be used to decontaminate air and other gas flows, in addition to solid objects. FIG. 9 illustrates an embodiment wherein the decontamination apparatus 38 is used in the manner of a gas mask to furnish decontaminated breathing air for a person. The enclosure 56 is structured as a cannister having an air intake and an outlet providing air to a face mask 66 placed over the face of a person. The cleaning fluid mist is injected into the incoming air by the mist generator 42. The activator 46 may be positioned to activate the cleaning fluid mist in the manner of FIG. 2. Instead, in this case the activator 46 is positioned downstream of the air intake so that the cleaning fluid mist is first thoroughly mixed with the incoming air and thereafter activated by the activator 46. The filter 64 is provided as discussed earlier to remove particulate and any liquid remnants of the mist.

Some embodiments of the present disclosure operate in an ambient pressure of about one atmosphere or slightly above one atmosphere, all of which are within the scope of "substantially one atmosphere ambient pressure". As noted earlier, this capability is important because most decontamination situations require the ability to achieve the decontamination without setting up vacuum chambers or pressure chambers. The mist generator produces a small overpressure of the mist as it enters the one atmosphere environment, but does not require either a vacuum or a pressure chamber. Especially in embodiments such as those of FIGS. 3, 4, 6, 8, and 9, particulate matter may be removed from the contaminated region or contaminated gas flow and collected on filters, thereby removing the carrier medium of the microbiological organisms as well as destroying the exposed microbiological organisms themselves.

Decontamination Method

One aspect of the application relates to a method for decontaminating an article or substantially enclosed space, comprising the steps of: shearing a cleaning fluid into a mist comprising aerosol droplets accumulating in a top chamber portion of a substantially closed chamber comprising a funnel shaped top chamber portion, a bottom chamber portion, a side chamber portion and an interior chamber portion, wherein the cleaning fluid is sheared by ultrasonic cavitation; subjecting the mist to a nonthermal plasma actuator to form plasma activated ionic particles; and contacting the article or substantially enclosed space to the plasma activated ionic particles. One of ordinary skill will understand that the form, such as a funnel shaped top chamber, or factor of the aerolized method of applying plasma activated ionic particles is not limiting on the application.

Another aspect of the application relates to a method for decontaminating an article or substantially enclosed space, comprising the steps of: shearing a cleaning fluid into a mist comprising aerosol droplets by cavitating the cleaning fluid using an ultrasonic cavitator submerged in a substantially closed chamber comprising the cleaning fluid; subjecting the mist to a nonthermal plasma actuator in an outlet tube extending from an opening in a top chamber portion of the substantially closed chamber, wherein the outlet tube comprises a hollow lumen with a distal opening above the top chamber portion for expelling the aerosol droplets to form plasma activated ionic particles; and contacting the article or substantially enclosed space to the plasma activated ionic particles.

A further aspect of the application is a method for decontaminating an article or substantially enclosed space, comprising the steps of: submerging an ultrasonic cavitator in a reservoir of a cleaning fluid; cavitating the cleaning fluid with ultrasonic vibrations produced by the ultrasonic cavitator; generating a mist comprising aerosol droplets, wherein the mist is generated from the cleaning fluid while the cleaning fluid is being cavitated; subjecting the mist to a nonthermal plasma actuator to form plasma activated ionic particles; and contacting the plasma activated ionic particles to a pathogen.

Another aspect of the application relates to a method for decontaminating an article or substantially enclosed space, comprising the steps of: providing a reservoir of a cleaning fluid; cavitating the reservoir of cleaning fluid by applying force to the cleaning fluid; generating a mist comprising aerosol droplets, wherein the mist is generated from the cleaning fluid while the cleaning fluid is subject to cavitation by force; subjecting the mist to a nonthermal plasma actuator to form plasma activated ionic particles; and contacting the plasma activated ionic particles to a pathogen.

The present disclosure provides a method of decontaminating an article or substantially enclosed space by ultrasonic cavitation. The present application discloses that the use of ultrasonic cavitation within the cleaning fluid unexpectedly results in a low pressure, low fluid flow mist that significantly enhances kill performance and the ability to decontaminate tightly enclosed environments once the mist has been activated. The method also advantageously reduces the complexity of the machinery used in decontaminating processes as no air compression is required.

Decontamination Devices

Exemplary decontamination devices/systems of the present disclosure comprise an applicator having a cold plasma arc that splits a hydrogen peroxide-based solution into reactive oxygen species, including hydroxyl radicals, that seek, kill, and render pathogens inactive. The activated particles generated by the applicator kill or inactivate a broad spectrum of pathogens and are safe for sensitive equipment. In general, decontamination devices/systems of the present disclosure allow the effective treatment of an exemplary space measuring 104 $m^2$ in about 75 minutes, including application time, contact time, and aeration time. Decontamination devices/systems of the present disclosure are scalable and configurable to be effective in any size or volume of space/room/chamber/container. The scalability may be accomplished by the size of the device, by the manual control of the decontamination fluid, or by programming the air pressure of the device and the consequent fluid flow rate as a function of the input space/room/chamber/container parameters.

Exemplary spaces include, but are not limited to, clean rooms, research laboratories, production environments, service & technical areas (HEPA filters), material pass-through rooms, corridors and thoroughfares. The decontamination devices/systems of the present disclosure are applicable to areas from a single space to an entire building. The plasma activated ionic particles generated by the present device or system are non-caustic and silver free. In general, the mist generated by the present device or system moves through an enclosed space or over a surface. Exemplary surfaces that can be decontaminated include, but are not limited to, safety cabinets, general laboratory equipment, isolators, HEPA filters, Vivarium caging, and decommissioned equipment.

Another aspect of the present application relates to miniature decontamination devices that comprise a DCV miniature transformer and/or a DCV miniature compressor to reduce power demand and overall weight and size of the device. In some embodiments, a miniature decontamination device has that may be lunchbox-sized to backpack-sized, and/or has a weight in the range of 10-40 lb. In some embodiments, the miniature decontamination device is placed in a backpack, a lightweight portable case or on a wheeled cart. In certain embodiments, the device comprises a small chamber system that heats the decontaminating solution to cause vaporization before passing through the arc system. In particular embodiments, the device comprises a rechargeable battery operated portable wheeled system (similar in form to an IV stand-type system).

In some embodiments, the DCV miniature transformer has an input DC voltage in the range of 6-36V and generates an output of 12-22.5 kV. In some embodiments, the DCV miniature transformer has an input DC voltage of 24V and generates an output of 17.5 kV.

In some embodiments, the DCV miniature compressor provides a pressure in the range of 10-60 psi and has an input DC voltage in the range of 6-36V. In some embodiments, the DCV miniature compressor provides a pressure in the range of 30-40 psi and has an input DC voltage of 24V.

In some embodiments, the miniature decontamination device further comprises a diode/capacitor rectifier that smooths out arc converting process and increases the converting efficiency in AC.

In some embodiments, the miniature decontamination device further comprises low flow pump with a flow rate in the range of 4-40 ml/min and an operating voltage in the range of 6-36 VDC.

In some embodiments, the miniature decontamination device further contains a control module that allows control (e.g., start and or stop the device) and monitoring of the miniature decontaminating device from a remote device such as a tablet or a phone. In some embodiments, the control module further controls data storage, transfer and printing.

Another aspect of the present application relates to a miniature decontamination device that comprises a miniature transformer and an ultrasonic wafer or ultrasonic nebulizer as a mist generator. In some embodiments, the mist generator comprises a substantially closed sonication chamber that comprises a funnel shaped top chamber portion, a bottom chamber portion, a side chamber portion and an interior chamber portion, wherein the cleaning fluid is sheared by ultrasonic cavitation within the sonication chamber. In some embodiments, the device comprises more than one ultrasonic wafer. In some further embodiments, the device comprises 2, 3, 4, 5, 6, 7, 8, 9, or 10 ultrasonic wafers.

In some embodiments, the decontamination device has a modular structure that reduces the footprint of the device and allows exchange of modules between different devices.

In some embodiments, the decontamination device further comprises low flow pump with a flow rate in the range of 4-40 ml/min and an operating voltage in the range of 6-36 VDC or 10-28 VDC.

In some embodiments, the decontamination device further contains a control module that allows control (e.g., start and or stop the device) and monitoring of the miniature decontaminating device from a remote device such as a tablet or a phone. In some embodiments, the control module further controls data storage, transfer and printing. In some embodiments, the control module allows for remote service and connection, for recording video or data, and for providing feedback to the user during use or after use.

Figure 10A:
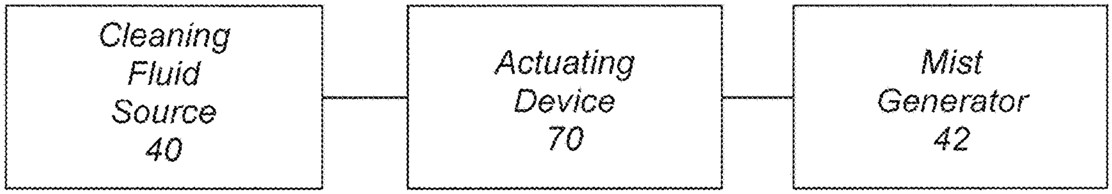
FIG. 10A represents a configuration of device elements wherein a cleaning fluid source 40 and a mist generator 42 are linked via an actuating device 70 that has an adjustable range of rotation of up to 360 degrees.
Figure 10B:
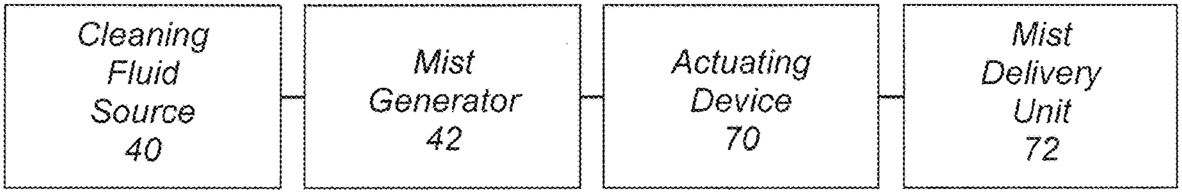
FIG. 10B represents a configuration of device elements wherein a cleaning fluid source 40 is interfaced with a mist generator 42 that, in turn, is linked to a mist delivery unit 72 via an actuating device 70 that has an adjustable range of rotation of up to 360 degrees.
Figure 10C:
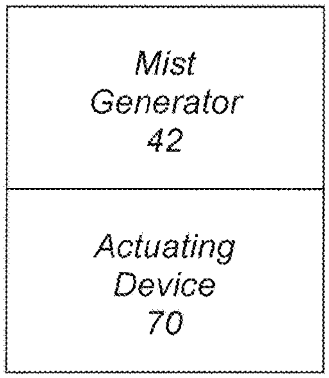
FIG. 10C represents a configuration of device elements wherein a mist generator 42 is mounted on an actuating device 70 that has an adjustable range of rotation of up to 360 degrees.
Figure 10D:
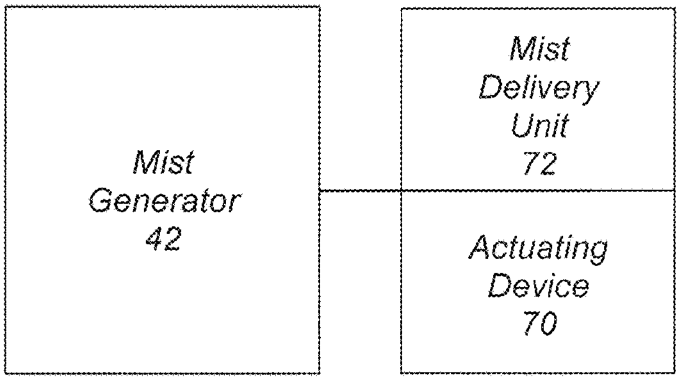
FIG. 10D represents another configuration of device elements wherein a mist generator 42 feeds into a mist delivery unit 72 that is mounted on an actuating device 70 that has an adjustable range of rotation of up to 360 degrees.

In some embodiments, the decontamination device is mounted on a rotating base that allows better coverage for the area to be decontaminated, as illustrated in the diagrams of FIGS. 10A-D. In some embodiments, the rotating base is a 180-degree rotating base. In some embodiments, the rotating base is a 360-degree rotating base. In some embodiments, the rotating base is an adjustable rotating base having a rotation range of 60-360 degrees. In some embodiments, the rotation is around a single axis. In other embodiments, the rotation is around multiple axes. In still other embodiments, the rotation is in all directions or is a fully spherical motion. FIG. 10A represents a configuration of device elements wherein a cleaning fluid source 40 and a mist generator 42 are linked via an actuating device 70 that has an adjustable range of rotation of up to 360 degrees. FIG. 10B represents a configuration of device elements wherein a cleaning fluid source 40 is interfaced with a mist generator 42 that, in turn, is linked to a mist delivery unit 72 via an actuating device 70 that has an adjustable range of rotation of up to 360 degrees. FIG. 10C represents a configuration of device elements wherein a mist generator 42 is mounted on an actuating device 70 that has an adjustable range of rotation of up to 360 degrees. FIG. 10D represents another configuration of device elements wherein a mist generator 42 feeds into a mist delivery unit 72 that is mounted on an actuating device 70 that has an adjustable range of rotation of up to 360 degrees.

Figure 11A:
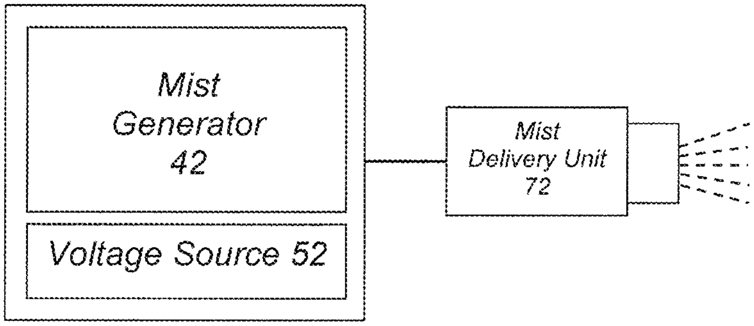
FIG. 11A depicts an embodiment wherein at least a mist generator 42 and a voltage source 52 are contained within a portable housing. The mist generator is functionally connected to a mist delivery unit 72 which may be mounted on the housing or is a remote unit.
Figure 11B:
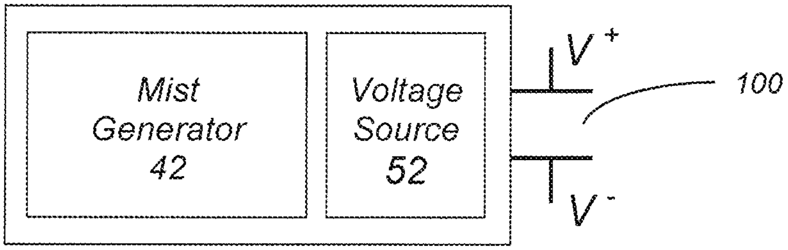
FIG. 11B depicts a mist generator 42 and a voltage source 52 contained within a portable container, wherein the entire unit can be hand held, mounted on another apparatus, or held by/mounted on another machine or a robot.
Figure 11C:
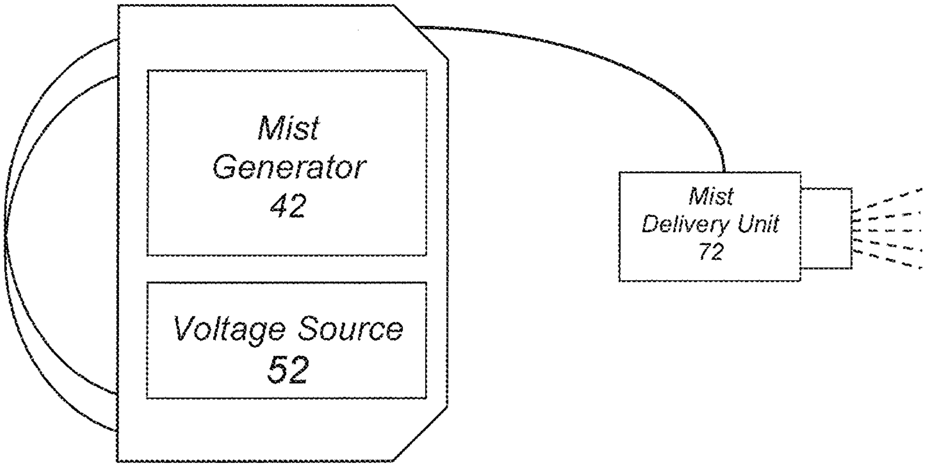
FIG. 11C depicts an exemplary embodiment wherein a mist generator 42 and a voltage source 52 are contained within a wearable container, such as a back pack.

FIGS. 11A-C depict exemplary embodiments of the decontamination device that are mobile or portable. The depictions are not intended to show the elements of the device in a fixed position within the portable units, rather the placement of individual components as show is merely exemplary and the positions of the elements can be rearranged to suit a particular application. FIG. 11A depicts an embodiment wherein at least a mist generator 42 and a voltage source 52 are contained within a portable housing. In some embodiments, the voltage source 52 is AC. In other embodiments, the voltage source 52 is DC. In still other embodiments, the voltage source 52 can be switched between AC and DC. The mist generator 42 is functionally connected to a mist delivery unit 72 which may be mounted on the housing or is a remote unit. In some embodiments, the mist delivery unit 72 is hand held, mounted on another apparatus, or held by/mounted on another machine or a robot. In some further embodiments, the robots are self-navigating and patrol an area. FIG. 11B depicts a mist generator 42 and a voltage source 52 contained within a portable container, wherein the entire unit can be hand held, mounted on another apparatus, or held by/mounted on another machine or a robot. In some embodiments, the voltage source is AC. In other embodiments, the voltage source 52 is DC. In still other embodiments, the voltage source can be switched between AC and DC. In particular embodiments, the mist is dispersed from the unit via high voltage actuation 100. In some embodiments, the high voltage actuation is persistent. In other embodiments, the high voltage actuation is intermittent. In particular embodiments, the high voltage actuation charges the mist and further atomizes the droplets. FIG. 11C depicts an exemplary embodiment wherein a mist generator 42 and a voltage source 52 are contained within a wearable container, such as a back pack. The mist generator 42 is functionally connected to a mist delivery unit 72 which may be mounted on the container or is a remote unit. In some embodiments, the mist delivery unit 72 is hand held, mounted on another apparatus, or held by/mounted on another machine or a robot.

Figure 12A:
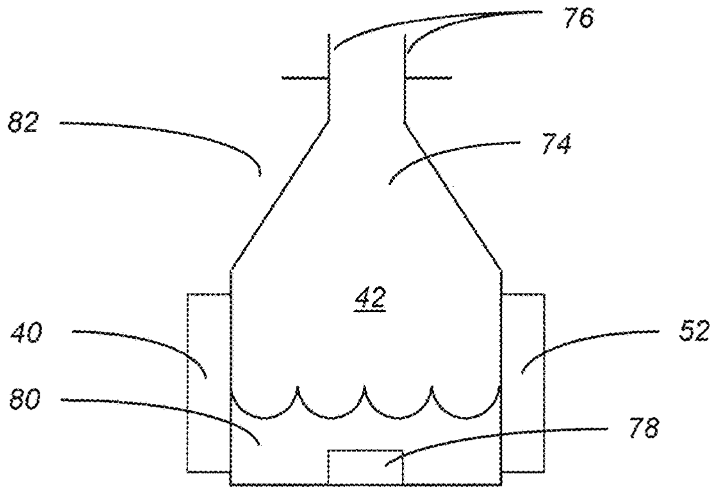
FIG. 12A illustrates the decontamination device comprises an ultrasonic wafer 78 or ultrasonic nebulizer as a mist generator.

As exemplified in FIG. 12A, in some embodiments, the decontamination device comprises an ultrasonic wafer or ultrasonic nebulizer 82 as a mist generator. In some embodiments, the mist generator 42 comprises a substantially closed sonication chamber that comprises a bottom chamber portion or reservoir, a top chamber portion 74 forming a pathway between the bottom chamber portion and a plasma actuator 76, a voltage source 52, a side chamber portion comprising a cleaning fluid source 40 and an interior chamber portion, wherein the cleaning fluid 80 that is dispensed into the nebulizer 82 is sheared by ultrasonic cavitation generated by a ultrasonic cavitation device 78 within the sonication chamber. The cleaning fluid 80 is introduced into a fluid chamber or reservoir until it submerges an ultrasonic cavitator 78. The ultrasonic cavitator 78 produces resonant ultrasonic waves that serve to cavitate the cleaning fluid, which produces a mist of aerosol droplets that rise from the fluid through a pathway 74. The mist passes through an applicator head and a plasma actuator, or electrodes 76, where the particles are activated before entering the external atmosphere. In some embodiments a fan may be used to direct the flow of the mist. In certain embodiments, the device comprises a rotating applicator based with a small circulating fan. In other embodiments, the device comprises a self-contained applicator that would include air compressor, fluid pump, and transformer. In some embodiments, heating elements heat the space inside to spread the nebulized mist. In some embodiments, the device comprises rotating heads or nozzles.

The pathway can take any form suitable to direct the aerosol droplets from the reservoir to the plasma actuator 76. In some embodiments, the pathway is in the form of a funnel. In other embodiments, the pathway may be, but is not limited to, in the form of a pipe, tube, elbow or cylinder.

In some embodiments, the plasma actuator is nonthermal. In other embodiments, the plasma actuator is thermal.

Figure 12B:
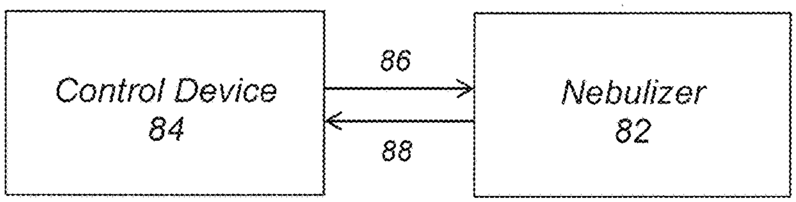
FIG. 12B diagrams a system wherein a mobile/wireless/remote control device 84 is functionally connected to a decontamination device of the present disclosure, such as a nebulizer 82.
Figure 12C:
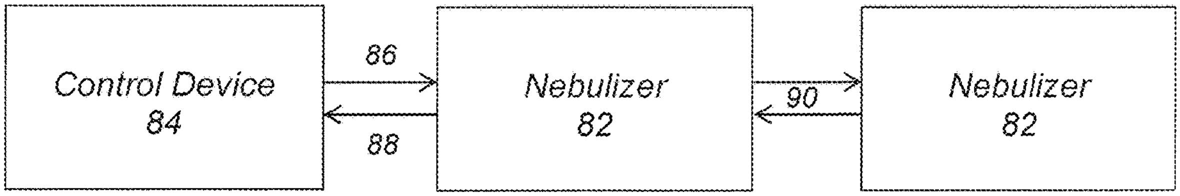
FIG. 12C diagrams an embodiment of the system, wherein the system comprises multiple decontamination devices, such as nebulizers, that are controlled by a control device 84 and further communicate between the nebulizers 82 by wired or wireless means. Information from individual nebulizers 82 can be fed back to the control device 84 either en masse or individually. For example, the dosages emitted by two different nebulizers 82 may start or complete at different times and the data can be reported independently.

FIG. 12B diagrams a system wherein a mobile/wireless/remote control device 84 is functionally connected to a decontamination device of the present disclosure, such as a nebulizer 82. The functional connection can be wired or wireless. In some embodiments, a wireless connection includes, but is not limited to, radio frequency, infrared, wifi, BLUETOOTH, or any other suitable means of wireless communication. In some embodiments, the control device 84 sends control instructions 86 to the nebulizer 82 via the functional connection and the nebulizer 82 send feedback data 88 to the control device 84 via the functional connection. FIG. 12C diagrams an embodiment of the system, wherein the system comprises multiple decontamination devices, such as nebulizers 82, that are controlled by a control device 84 and further two-way communicate 90 between the nebulizers 82 by wired or wireless means. In some embodiments, a system can have a single control unit 84 that controls multiple nebulizers 82 that are situated in different areas of a room, and/or different rooms, and or/attached to, or aimed at, different pieces of equipment, such as a flow hood, that need to be sterilized/decontaminated. One of ordinary skill will understand that the devices may be networked to the control unit individually, or sequentially, or wirelessly, and that the network arrangement depicted herein is not limiting.

Figure 13A:
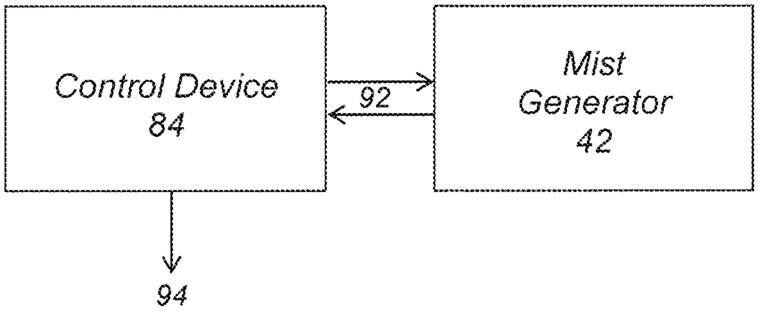
FIGS. 13A-B illustrates a similar system having a single (FIG. 13A) or multiple (FIG. 13B) mist generator(s) 42 being controlled by a control device 84, which further provides data 94 to an external source regarding the treatment of an area or surface.
Figure 13B:
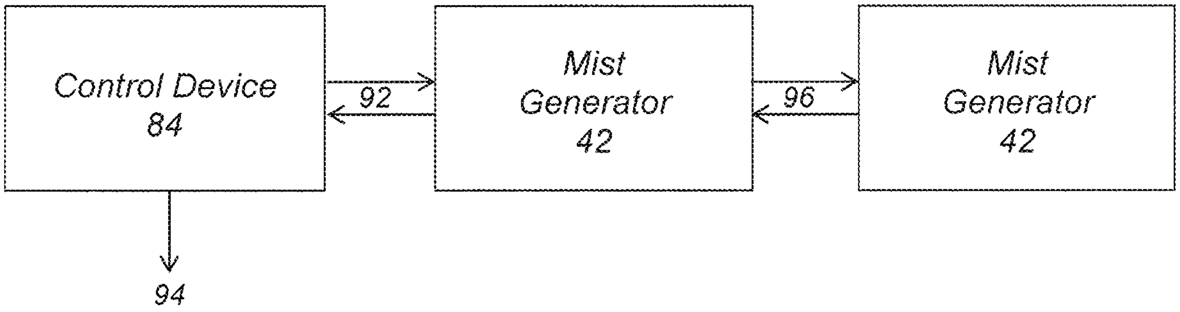

FIGS. 13A-B depict a similar system having a single (FIG. 13A) or multiple (FIG. 13B) mist generator(s) 42 which two-way communicate 92, 96, being controlled by a control device 84, which further provides data 94 to an external source regarding the treatment of an area or surface. One of ordinary skill will also understand that the devices may be networked to the control unit individually, or sequentially, or wirelessly, and that the network arrangement depicted herein is not limiting.

Figure 14:
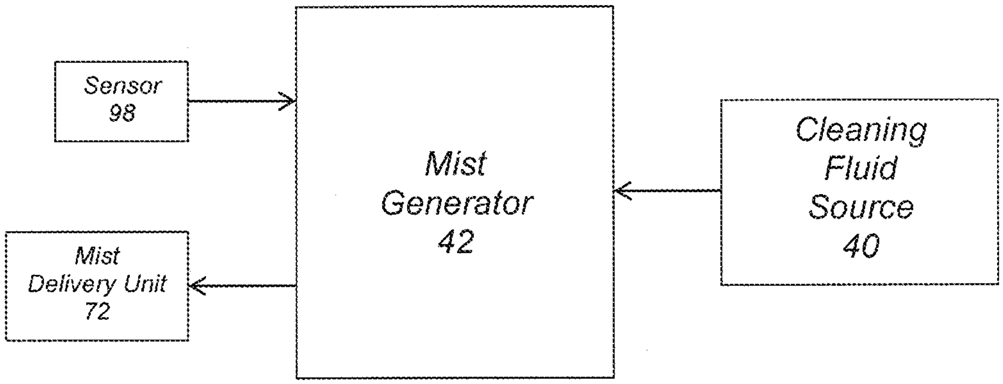
FIG. 14 illustrates a system wherein a mist generator 42, cleaning fluid source 40 and mist delivery unit 72 are further interfaced with a sensor 98.

FIG. 14 diagrams a system wherein a mist generator 42, cleaning fluid source 40 and mist delivery unit 72 are further interfaced with a sensor 98. In some embodiments, the sensor 98 detects microbes (such as bacteria, parasites, amoebae, or viral particles), that are airborne or contaminating a surface. In some embodiments, the sensor 98, upon detection of contaminants, automatically triggers actuation of the system.

Figure 15:
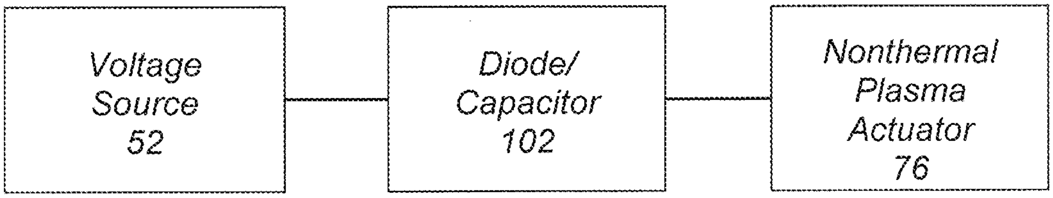
FIG. 15 diagrams an exemplary rectifier for forming free radicals, comprising a voltage source 52, at least one diode/capacitor 102 interfaced with a plasma actuator 76.

Another aspect of the present application relates to a decontamination device that comprises a diode/capacitor rectifier that smooth's out arc converting process and increases the converting efficiency. FIG. 15 diagrams an exemplary rectifier comprising a voltage source 52, at least one diode/capacitor 102 interfaced with a nonthermal plasma actuator 76.

Conventional methods of decontamination are less effective in decontaminating small enclosures. This application discloses that decontamination using a very dry mist comprising ionized hydrogen peroxide provides unexpectedly high levels of kill rate of pathogens (which encompasses bacteria, fungi, protozoan or viruses), such as, e.g., *Candida auris*, in small enclosures, semi-enclosed spaces and closed areas (a small enclosure is an area of 12"×12"×12" or less; a semi-enclosed space is an area in which part of a small enclosure is open to other areas; a closed area is an area in which no parts of the small enclosure are open to other areas).

A very dry mist is a mist in which particles have particle size diameter within the ranges of about 0.1-0.2 microns, 0.1-0.3 microns, 0.1-0.4 microns, 0.1-0.5 microns, 0.1-0.6 microns, 0.1-0.7 microns, 0.1-0.8 microns, 0.1-0.9 microns, 0.1-1 microns, 1-1.1 microns, 1-1.2 microns, 1-1.3 microns, 1-1.4 microns, 1-1.5 microns, 1-1.6 microns, 1-1.7 microns, 1-1.8 microns, 1-1.9 microns, 1-2 microns, 0.5-0.6 microns, 0.5-0.7 microns, 0.5-0.8 microns, 0.5-0.9 microns, 0.5-1 microns, 0.5-1.1 microns, 0.5-1.2 microns, 0.5-1.3 microns, 0.5-1.4 microns, 0.5-1.6 microns, 0.5-1.7 microns, 0.5-1.8 microns, 0.5-1.9 microns, 0.5-2 microns, 0.5-2.1 microns, 0.5-2.2 microns, 0.5-2.3 microns, 0.5-2.4 microns, 0.5-2.5 microns, 0.5-2.6 microns, 0.5-2.7 microns, 0.5-2.8 microns, 0.5-2.9 microns, 0.5-3 microns, 0.5-3.1 microns, 0.5-3.2 microns, 0.5-3.3 microns, 0.5-3.4 microns, or 0.5-3.5 microns. In certain embodiments, the very dry mist has particles with particle diameter size in the range of about 0.5-3 microns.

An aspect of this application discloses the use of a handheld, point-and-spray device that may be used for decontamination of small enclosures by using a very dry mist comprising ionized hydrogen perodice. The handheld device includes a programming clock, and provides air pressure control and fluid flow control through use of one or more potentiometers. The programming clock provides the ability to automate cycles of decontamination within a small enclosure. The cycles of decontamination controlled by the programming clock may, for example, include cycles of spraying a very dry mist for thirty seconds, stopping spray for ten seconds, and then re-starting spraying for another thirty seconds, etc, repeating such cycles for a fixed period of time. The programming clock can be set manually by a user or controlled remotely by wireless by the user or a computer processor with pre-programmed decontamination cycles that are transmitted to the device for deployment. In certain embodiments, a user may manually control the cycles of decontamination by operating by hand the control knob of the device which controls spray of the very dry mist.

In certain embodiments, the device will possess a computer processor that can calculate the appropriate settings (e.g. flow rate, air pressure, number and length of decontamination cycles) to produce a very dry mist comprising ionized hydrogen peroxide that will effectively decontaminate a small enclosure. In such embodiments, the user may enter the parameters of the small enclosure manually to the device, or enter them remotely by a wireless connection. The operation of the device can be fully automated, fully manually controlled, or may be semi-automated (e.g., uses cycles of decontamination performed automatically according to parameters that have been manually entered).

Figure 16:
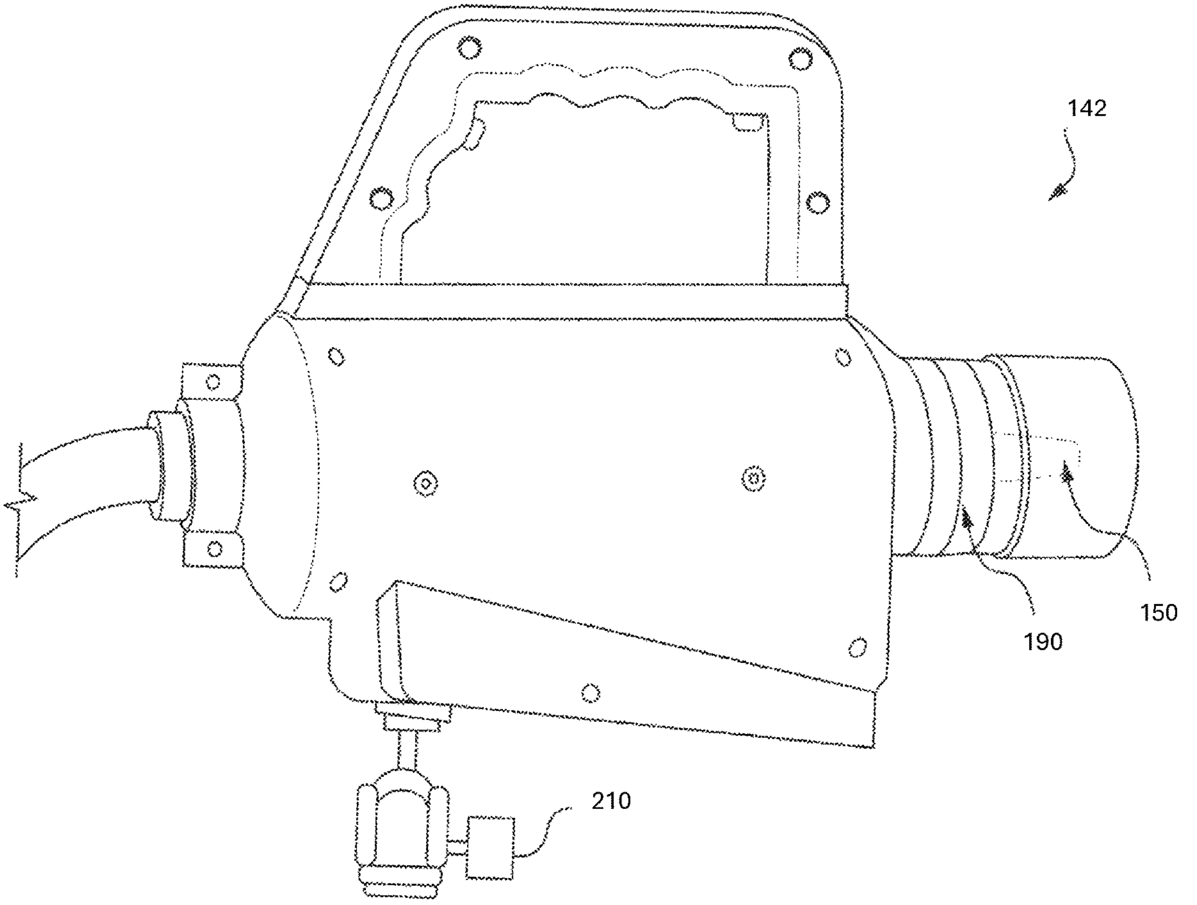
FIG. 16 depicts an embodiment of a mist generator 142 operable manually as a hand-held device and programmable for automated operation.

FIG. 16 illustrates one embodiment of a cleaning fluid source, specifically a mist generator 142, which operates on two platforms. One platform may be a handheld, point-and-spray surface decontamination device, and the other platform may be a programmable, automated environment decontamination device designed for small enclosures. The handheld, point-and-spray feature allows for manual or automated control of the decontamination action. The programmable automation may allow input of the surrounding parameters in order to predictably and consistently operate in an optimal arrangement with the geometry of the decontaminated enclosure.

Figure 17:
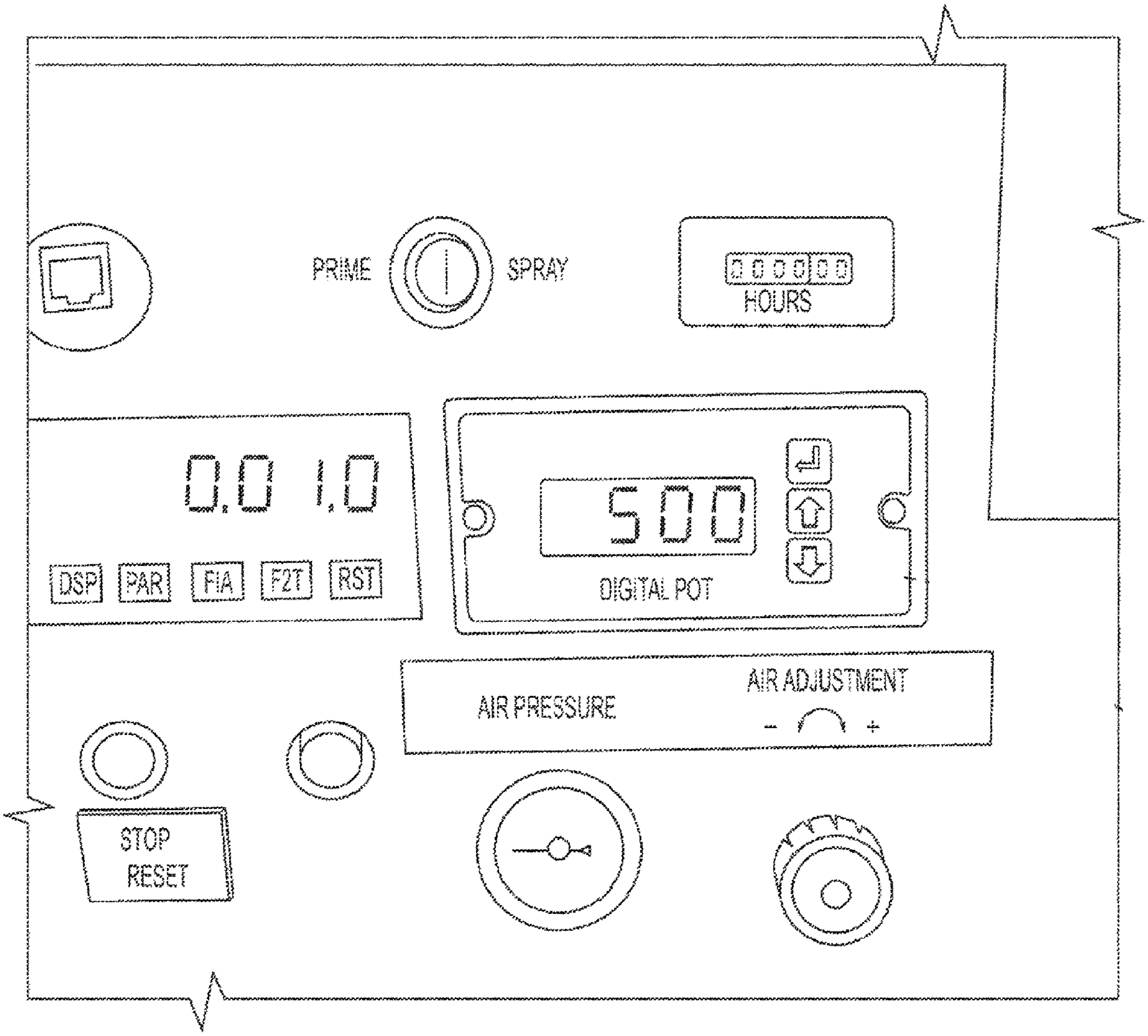
FIG. 17 depicts an embodiment of a display of a programming clock 143 regulating fluid properties of a fluid applied by a mist generator device.

FIG. 17 illustrates one embodiment of a display of a programming clock 143 adjustable to control a mist generator 142 shown in FIG. 16, for example. A voltage source within the decontamination device may be connected to an adjustable voltage divider, such as a potentiometer, for example. The potentiometer may include a housing that contains a resistive element and a contact that slides along the resistive element, two electrical terminals at the two ends of the resistive element, and a mechanism that moves the sliding contact from one end to the other. The potentiometer used may be a circular slider potentiometer, a liner slider potentiometer, or any other suitable slider arrangement may be used. The potentiometer may include a resistive element made of graphite, plastic containing carbon particles, resistance wire, or a mixture of ceramic and metal, for example.

The potentiometer may be controlled by a control unit in order to regulate inputs for the electric circuit of the voltage source. The potentiometer may allow a user to control the air pressure and the fluid flow rate of the cleaning fluid mist flowing through a tube 150. While the reduced air pressure affects the size of the produced mist/fog particles, the tube 150 may be modified into a funnel nozzle to compensate for the reduction. The tube's transverse diameter may be gradually varied to allow the spray of the decontamination fluid through the tube 150 to be adjusted in order to produce a desired mist/fog particle size.

The voltage source may be a battery and a circuit to supply a high voltage to an activation source for a sufficient period to activate the amount of cleaning fluid that is stored within a pressure container. As mentioned above, the tube 150 may be either the nozzle of the pressure container or it may be funnel shaped. As shown in FIG. 16, the tube 150 may be attached to the hand-held device 142 operating from a cleaning fluid source and with a plug-in or battery electrical voltage source. The cleaning fluid source may be pressurized to drive the flow of the cleaning fluid through the tube 150, or there may be provided an optional pump that forces the cleaning fluid through the mist generator 142 and out of the tube 150 with greater force.

As shown in FIG. 16, the decontamination device 142 may be mounted on a rotating base that allows better coverage for the area to be decontaminated. The rotating base may be a 180-degree rotating base, or a 360-degree rotating base. In some embodiments, the rotating base is an adjustable rotating base having a rotation range of 60-360 degrees. In some embodiments, the rotation is around a single axis. In other embodiments, the rotation is around multiple axes. In still other embodiments, the rotation is in all directions or is a fully spherical motion. In yet another embodiment, a knob 210 may be applied for manual regulation of the air pressure and fluid flow rate.

In a programmable device, the control unit may be programmed to control the potentiometer and the pump based on the desired fluid parameters. For example, in particularly small enclosures, a drier mist is generated, in order for the mist to travel a shorter distance. This may be accomplished by reducing the air pressure of the decontamination device well below the predetermined standard air pressure, or the standard fluid flow rate well below the predetermined standard flow rate. The standard air pressure entered into the programmable control unit may be in the range between 25-50 psi, and the input standard air pressure range may be modified as deemed suitable. Moreover, the standard fluid flow rate entered into the programmable control unit may be in the range between 25-50 ml/minute, and the input standard fluid flow rate range may be modified as considered appropriate.

In some embodiments, the air pressure of the decontamination device may be 5-25 psi, or, in alternative embodiments, it may be 10-20 psi. In one example discussed in detail below, the air pressure of the decontamination device is 15 psi. Additionally, in certain embodiments, the flow rate of the decontamination fluid may be 5-25 ml/minute, or, in alternative embodiments, it may be 10-15 ml/minute. In one example discussed in detail below, the flow rate of the decontamination fluid is 10 ml/minute.

08 In certain embodiments, the spray pattern of a cleaning fluid may be set based on spray cycle parameters, such as a time period during spraying, a time period between two consequent sprayings, and a total number of sprayings performed. In certain embodiments, the time period between two consequent sprayings may be 10-120 seconds, or, in alternative embodiments, it may be 30-90 seconds. In one example discussed in detail below, the time period between two consequent sprayings is 60 seconds. Moreover, in certain embodiments, the time period during sprayings may be 10-180 seconds, or, in alternative embodiments, it may be 60-120 seconds. In some cases, the time period during spraying is 90 seconds, with 60 second intervals between spraying.

In comparison with the programmable device, a handheld surface decontamination device may be manually operated by turning the control knob on a handheld applicator to produce the ionized hydrogen peroxide very dry mist. In one example, fluid or air settings are not programmably modified, but are, instead, manually controlled by the user based on an assessment by the user of the actual confines of the small enclosure.

One embodiment of the hand-held device 142 is used in conjunction with a small enclosure to achieve decontamination of the interior of the small enclosure. The small enclosure may serve as a chamber in which a target object is decontaminated. The target object may be stationary, or it may move through the enclosure on a conveyer. The small enclosure may be defined with respect to the device 142 by a variety of characteristics, such as: the dimensions of the enclosure, the relative position of the device 142 from the boundaries of the enclosure, the air temperature/pressure/humidity within the enclosure, or any other property of the enclosure space deemed relevant. Moreover, in instances where a target object moves within the small enclosure, an initial location of the object, its relative speed, and its moving direction in regard to the device 142 may be measured to be used as input subsequently. In instances where the device 142 rotates around a fixed position within the small enclosure, the rotation speed may be ascertained and used as input for processing by a computer processor.

The device 142 may be integrated into a system for decontaminating. The input of the small enclosure, and any target object characteristics, with respect to the device 142 may be entered into the system manually, or it may be measured by multiple sensors. The sensors may be in networked communication with the computer processor, such as a control unit programmed to control the device 142. The control unit may control an adjustable potentiometer that regulates parameters relevant to the decontamination cycle of the device 142.

In one example, the ionized hydrogen peroxide mist added to and mixed with another gas flow. The activated cleaning fluid mist mixes with the gas flow, and the mixed gas flow contacts the surface of the small enclosure and/or target object. Some of the parameters relevant to the performance of the decontamination device 142 may be air pressure of the gas that mixes with the mist and fluid flow rate of the fluid departing the device 142. These parameters may be regulated by controlling an air valve 190 placed on the front of the device 142, and/or by modifying the size and shape of the tube 150, for example.

As shown in FIG. 17, the fluid parameters of the decontamination device 142 may be monitored on the display of the device. The parameters may be adjusted remotely. In one embodiment, a wireless network connection is feasible between the control unit and the device 142, in order to set the fluid parameters of the device 142. In some embodiments, a wireless connection includes, but is not limited to, radio frequency, infrared, wifi, BLUETOOTH, or any other suitable means of wireless communication.

The adjustment of the fluid parameters is particularly important in small enclosures. A mist producing device 142 allows for manipulation of fluid flow rates and air pressure as needed to accommodate unique settings required for very small spaces. Very small enclosures require that the mist/fog being dispensed only travels far enough to reach across the longest dimension of the enclosure, or to reach the target object, for example. The fluid parameters adjustment may be accomplished with the air valve 190, and may be verified with a air pressure gauge also located on the front of the unit, for example.

It is a common problem of the conventional technology that excessive air pressure reduction produces mist particles that are too large to achieve a desired mist/fog profile. At the same time, particularly small enclosure spaces often require significant air pressure reduction. These opposing constraints of a decontamination system are addressed by certain embodiments of the present disclosure. Namely, by programming the processor to control the potentiometer based on the input parameters of the small enclosure, a user can regulate a fluid flow rate in synchronization with the air pressure. As a result, reducing the fluid flow rate while simultaneously lowering the air pressure maintains the mist/fog particle size small, while limiting the distance the spray can reach. In this manner, the mist sprayed by the device 142 remains within the boundaries of the small enclosure, without creating excessively wet and dense fog. The programmable balance between the air pressure and the fluid flow rate, therefore, prevents saturating surfaces opposite to mist applicators, increased moisture accumulation due to condensation, false negative validation results or increased aeration times of the enclosure.

In the alternative, the device 142 can produce all of the identified benefits if manually controlled, as well. Namely, a hand-held platform of the decontamination device 142 allows operation by using a control knob on the handheld applicator to produce the ionized hydrogen peroxide mist. In certain embodiments, the device is designed to be used by technicians using a trigger on the device to control its use by adjusting the position of the trigger. In other embodiments, the operation of the device may be fully automated or semi-automated. Desired values achieved manually may be monitored on the device display.

Decontamination devices/systems may be scalable and configurable to be effective in any size or volume of space/room/chamber/container. The scalability may be accomplished by the size of the device, by the manual control of the decontamination fluid, or by programming the air pressure of the device and the consequent fluid flow rate as a function of the input space/room/chamber/container parameters. Accordingly, the size and volume of the device 142 may be selected depending on the geometry of the enclosure and the location of the target object inside the enclosure in order to optimize decontamination performance.

In some embodiments, a miniature decontamination device 142 further contains a control module that allows control (e.g., start and or stop the device) and monitoring of the miniature decontaminating device from a remote device such as a tablet or a phone. In other embodiments, the control module further controls data storage, transfer and printing. In certain embodiments, the control module allows for remote service and connection, for recording video or data, and for providing feedback to the user during use or after use.

The following examples are by way of illustration only and should not be considered limiting on the aspects or embodiments of the application.

Example 1

In a first test series, identical cultures of *serratia marcenscens* were prepared by plating onto filter papers. One specimen was incubated for 24 hours at 30° C. in air as a control. Significant growth of the bacteria culture was observed. A second specimen was exposed to a 3 percent by volume aqueous hydrogen peroxide mist (which had not been activated) for 60 seconds in air at one atmosphere pressure, and thereafter incubated for 24 hours at 30° C. in air. Significant growth of the bacteria culture was observed. A third specimen was exposed to a 3 percent by volume aqueous hydrogen peroxide mist, which had been activated by passage through a 10.5 kilovolt AC arc, for 60 seconds in air at one atmosphere pressure, and thereafter incubated for 24 hours at 30° C. in air at one atmosphere pressure. This specimen showed no growth of the bacteria culture, which was killed by the treatment. After this demonstration that the activation treatment rendered the 3 percent hydrogen peroxide mist capable of preventing growth, additional respective specimens were tested using 1.5 percent, 0.75 percent, 0.3 percent, and 0 percent ("activated" water vapor only) concentration hydrogen peroxide mists for 60 seconds exposure in air at one atmosphere pressure, and incubated as described. The specimens contacted by the 1.5 percent and 0.75 percent hydrogen peroxide mists showed no growth. The specimen contacted by the 0.3 percent hydrogen peroxide mist showed very slight growth. The specimen contacted by the 0 percent hydrogen peroxide mist showed significant growth of the bacteria culture.

Example 2

For a second and third test series, a duct-simulation structure was built. The duct-simulation structure was a pipe about 10 inches in diameter and 10 feet long, oriented vertically. The mist generator and activator were positioned at the top of the pipe, and a fan operating at about 350-400 cubic feet per minute gas flow was positioned at the bottom of the pipe to induce a gas flow downwardly through the pipe. Test ports were located at 1 foot, 2 feet, 4 feet, and 6 feet from the top of the pipe, and specimens to be tested were inserted at the various ports.

In the second test series, bacterial spore strips (each about ¾ inch long and ¼ inch wide) impregnated with about $10^6$ spores per strip of *Bacillus stearothermophilus* were placed in each of the test ports of the duct-simulation structure. After testing, the specimens were incubated at 50° C. for seven days. In the first test specimen series, air only (no hydrogen peroxide) was flowed over the specimens for 15 seconds. Significant growth of the bacteria culture at all test ports was observed after incubation. In the second specimen series, a 6 percent by volume hydrogen peroxide mist was generated, but not activated, and flowed over the specimens for 15 seconds. The same significant growth of the bacteria culture at all test ports was observed as for the first test specimen series. In the third specimen series, this procedure was repeated, but the 6 percent hydrogen peroxide mist was activated by a 15 kilovolt AC arc. No growth of the bacteria culture was observed at any of the test ports. These results for *bacillus stearothermophilus* are significant, because this bacteria is known to be resistant to growth control using conventional, low percentage non-activated hydrogen peroxide treatments.

Example 3

In the third test series, bacterial spore strips like those described above were used, except that the bacteria was *Bacillus subtilis* var. *niger. Bacillus subtilis* var. *niger* is a recognized proxy for *Bacillus anthracis*, which is in the same genus and which causes anthrax. Because of its similarity to *Bacillus anthracis, Bacillus subtilis* var. *niger* is used in laboratory testing to study growth of anthrax and its control, without the risk of contracting or spreading anthrax. In the first test specimen series, air only (no hydrogen peroxide) was flowed over the specimens for 15 seconds. Significant growth of the bacteria culture was observed after incubation of specimens from all ports. In the second specimen series, a 6 percent by volume hydrogen peroxide mist was generated, but not activated, and flowed over the specimens for 15 seconds. The same significant growth of the bacteria culture was observed at all ports as for the first test specimen series. In the third specimen series, this procedure was repeated, but the 6 percent hydrogen peroxide mist was activated by passage through a 15 kilovolt AC arc. No growth of the bacteria culture was observed at any of the ports. This testing established that this approach controls the growth of the anthrax proxy in the duct simulation structure.

Example 4

In further testing, ultrasonic cavitation of the cleaning fluid to generate a low pressure, low air flow mist resulted in superior kill.

A 16×16×16 inch box was built for this testing, with the nozzle of the decontamination apparatus penetrating the bottom of the box in the center of the bottom panel.

6-Log biological (*Geobacillus stearothermophilus*) and chemical (iodine $H_2O_2$) indicators were placed in the center of all of the vertical panels. Biological and chemical indicators were also placed on the bottom panel of the box, immediately next to the nozzle.

Activated mist was injected into the box for one minute and allowed to dwell for five minutes.

The biological indicators were then removed from the box and incubated for 7 days. Following incubation, the biological indicators were examined and exhibited 6 log kill of the bacteria.

Although a particular embodiment has been described in detail for purposes of illustration, various modifications and enhancements may be made without departing from the spirit and scope of the application. Accordingly, the application is not to be limited by the described embodiments.

Example 5

In an efficacy test, the decontamination device/system of the present disclosure was tested against a variety of bacterial spores and gram-negative bacteria (including multiple drug resistant organisms, gram-positive bacteria, mold and viruses. Using procedures described in the present disclosure, the $\log^{10}$ reduction of the organisms in the following table were determined:

| Organism | Classification | Log Reduction |
|---|---|---|
| *Bacillus atrophaeus* (surrogate for *B. anthracic*) | Bacterial spore | >8.3 |
| *Geobacillus stearotherophilus* | Bacterial spore | >6.3 |
| *Bacillus subtilis* | Bacterial spore | >6.0 |
| *Clostridium difficile* | Bacterial spore | >6.0 |
| *Escherichia coli* | Gram Negative | >7.4 |
| *Pseudomonas aeruginosa* | Gram Negative | >6.0 |
| *Serratia marcescens* | Gram Negative | >6.0 |
| *Salmonella entercia* | Gram Negative | >5.5 |
| *Staphylococcus aureus* | Gram Positive | >7.4 |
| Methicillin- resistant *Staphylococcus aureus* | Gram Positive | >5.9 |
| *Bacillus atrophaeus* vegetative cells | Gram Positive | >9.0 |
| *Aspergillus niger* | Mold | >8.0 |
| *Aspergillus* species | Mold | >7.0 |
| *Cladosporium* species | Mold | >7.0 |
| *Penicillium* species | Mold | >7.0 |
| *Stachybotrys chartarum* | Mold | >7.0 |
| *Trichophyton mentagrophytes* | Mold | >6.0 |
| Human rhinovirus 16 (surrogate for human influenza) | Virus | >6.8 |
| Influenza A (H1N1) | Virus | >10 |
| Norovirus | Virus | >6.4 |
| Adenovirus | Virus | >5.8 |

The results presented in the table show that the decontamination device/system of the present disclosure is an effective broad-spectrum surface and air disinfectant/decontaminant. It is effective against, bacterial spores, gram-negative bacteria, gram-positive bacteria, multiple drug resistant organisms, mold and viruses. The decontamination device/system is effective for mold mitigation and remediation, as well as the elimination of bacteria and viruses.

The decontamination cycle discussed herein relates to the conversion of hydrogen peroxide solution to ionized hydrogen peroxide after passing through an atmospheric cold plasma arc. Ionized hydrogen peroxide contains a high concentration of reactive oxygen species composed mostly of hydroxyl radicals. Reactive oxygen species damage pathogenic organisms through oxidation of proteins, carbohydrates, and lipids. This leads to cellular disruptions and/or dysfunction and allows for disinfection/decontamination in targeted areas, including large spaces.

In certain embodiments for direct application onto surfaces, the particle size for the ionized hydrogen peroxide is 0.5-3 microns, flow rate is 50 ml per minute, dose application is 1 ml per square foot, with an application time of 5 seconds over per square foot of treatment area, and a contact time of 7 minutes to disinfect/decontaminate high touch surfaces. In particular embodiments, the solution used is formulated as silver, chlorine and peracetic acid free, which maximizes material compatibility on rubber, metals, and other surfaces. In other embodiments, effective whole room treatment can be achieved in under 45 minutes for a room which is over 3500 cubic feet. In such embodiments, flow rate may be 25 ml per minute per applicator used (which depends on room size), dose application is 0.5 ml per cubic foot. The room is safe to enter once hydrogen peroxide is below 0.2 ppm. Treatment time, dosage, dwell time, etc, can be varied to suit the desired decontamination goals of the user.

Example 6

In one example for direct application onto surfaces, a small enclosed space is decontaminated. The dimensions of the small container used for the treatment are 12" by 12" by 12". One of the objectives of the example is to maintain the particle size for the decontamination mist/fog sufficiently small (e.g., 0.5-3 microns) in order to avoid excessively dense fog resulting in increased moisture accumulation and aearation time, thus causing false negative validation results. In this example, four injections are performed with 60 seconds between each two consequent injections, and a pulsing program runs for approximately 90 seconds during each injection. Considering the reduced size of the container, the air pressure within the decontamination device is reduced well below the standard pressure range (e.g., 25-50 psi) to 15 psi. In order to prevent the pressure reduction from producing undesirably large sizes of mist/fog particles, the fluid flow rate is also reduced well below the standard range flow rate (e.g., 25-50 ml per minute) to 10-12 ml per minute. Treatment time, dosage, dwell time, etc, can be varied to suit the desired decontamination goals of the user. This very dry mist unexpectedly results in a enhanced kill rate of pathogens on surfaces of the small enclosure.

The above description is for the purpose of teaching the person of ordinary skill in the art how to practice the present application, and it is not intended to detail all those obvious modifications and variations of it which will become apparent to the skilled worker upon reading the description. It is intended, however, that all such obvious modifications and variations be included within the scope of the present application. The claims are intended to cover the claimed components and steps in any sequence which is effective to meet the objectives there intended, unless the context specifically indicates the contrary.

What is claimed is:

1. A method for decontaminating a semi-enclosed area, comprising the steps of:

entering input parameters of the semi-enclosed area into a processing unit, wherein the processing unit is programmed to determine fluid properties of a cleaning fluid in a decontamination device based on the input parameters of the semi-enclosed area space, wherein the decontamination device comprises a nozzle having an outlet and a tube, activating a decontamination cycle of the decontamination device, wherein the decontamination cycle comprises the steps of:

providing a reservoir of the cleaning fluid;

setting the determined fluid properties of the cleaning fluid;

generating a very dry mist comprising ionized hydrogen peroxide particles activated by a cold plasma arc, wherein the activated particles comprise a dissociated activated species that are hydroxyl radicals and which recombine to oxygen and water after contacting surfaces, and, wherein the very dry mist comprises particles of diameter size in the range of 0.5-0.9 microns, wherein the particle diameter size range is maintained by a coordinated setting of an applied air pressure and fluid flow rate, wherein the generated very dry mist is dispersed by high-voltage actuation at the nozzle outlet and applied within the semi-enclosed area at an applied air pressure of 5-25 pound-force per square inch (psi) measured as the static air pressure at the nozzle outlet during mist ejection as indicated on a device-mounted pressure gauge;

wherein the fluid flow rate is reduced concurrently with the applied air pressure to limit droplet travel to within a longest dimension of the semi-enclosed area while maintaining said particle diameter range; and wherein the decontamination device is a hand-held point-and-spray device.

2. The method of claim 1, further comprising operating the decontamination device manually.

3. The method of claim 1, wherein the input parameters of the semi-enclosed area comprise: dimensions of the semi-enclosed area space, a position of the decontamination device relative to boundaries of the semi-enclosed area space, air temperature, air pressure, and humidity of the semi-enclosed area, wherein the input parameters are adjusted under computer control responsive to the input parameters to preserve the 0.5-0.9 μm particle size while maintaining the applied air pressure at the nozzle outlet within 5-25 psi.

4. The method of claim 1, wherein the set fluid properties of the cleaning fluid comprise applied air pressure and fluid flow rate, wherein reducing applied air pressure below 25 psi is accompanied by reducing flow to maintain 0.5-0.9 μm particles.

5. The method of claim 4, wherein the fluid properties of the cleaning fluid are set by lowering the applied air pressure at the nozzle outlet and the fluid flow rate respectively below predetermined standard values to maintain 0.5-0.9 μm particle size and reduce spray travel within the semi-enclosed area.

6. The method of claim 1, wherein the setting of the determined fluid properties to the cleaning fluid is performed by controlling an air valve to maintain said particle size and applied air pressure at the nozzle outlet.

7. The method of claim 6, wherein the air valve is controlled by programming the processing unit to control a potentiometer.

8. The method of claim 1, wherein the size and shape of the tube at the nozzle outlet are adjusted under computer control responsive to input parameters of the semi-enclosed area to preserve the 0.5-0.9 μm particle size while maintaining the applied air pressure at the nozzle outlet within 5-25 psi.

9. The method of claim 1, wherein the input parameters of the semi-enclosed area are manually input.

10. The method of claim 1, wherein the input parameters of the semi-enclosed area are measured by a plurality of sensors that are in networked communication with the processing unit.

11. The method of claim 1, wherein the processing unit and the decontamination device are in wireless communication.

12. The method of claim 1, wherein the high-voltage actuation at the nozzle outlet further atomizes and electrically charges the droplets to maintain the 0.5-0.9 μm particle size at the applied air pressure at the nozzle outlet.

13. The method of claim 1, wherein the mist is applied in repeated spray cycles comprising a spray interval of 60-120 seconds followed by a pause interval of 30-90 seconds selected based on enclosure dimension and humidity.

14. A system for decontaminating a semi-enclosed area, comprising a decontamination device, wherein the decontamination device comprises a nozzle having an outlet and a tube, and a computer processor, wherein the computer processor is in networked communication with the decontamination device, wherein input parameters of the semi-enclosed area space are entered into the computer processor, wherein the computer processor is programmed to determine fluid properties of a cleaning fluid in the decontamination device based on the input parameters of the semi-enclosed area space, wherein the computer processor is further programmed to activate a decontamination cycle of the decontamination device, the decontamination cycle comprising the steps of:

providing a reservoir of the cleaning fluid;

setting the determined fluid properties of the cleaning fluid;

generating a very dry mist comprising ionized hydrogen peroxide particles activated by a cold plasma arc, wherein the activated particles comprise a dissociated activated species that are hydroxyl radicals and which recombine to oxygen and water after contacting surfaces, and, wherein the mist comprises particles of diameter size in the range of 0.5-0.9 microns, wherein the particle diameter size range is maintained by a coordinated setting of applied air pressure at the nozzle outlet and fluid flow rate, wherein the generated very dry mist is dispersed by high-voltage actuation at the nozzle outlet and applied within the semi-enclosed area at an applied air pressure at the nozzle outlet of 5-25 psi measured as the static air pressure at the nozzle outlet during mist ejection as indicated on a device-mounted pressure gauge;

wherein the fluid flow rate is reduced concurrently with the applied air pressure at the nozzle outlet to limit droplet travel to within a longest dimension of the semi-enclosed area while maintaining said particle diameter range; and wherein the decontamination device is a hand-held point-and-spray device.

15. The system of claim 14, wherein the decontamination device is operated manually.

16. The system of claim 14, wherein the input parameters of the semi-enclosed area comprise: dimensions of the semi-enclosed area, a position of the decontamination device relative to boundaries of the semi-enclosed area, air temperature, air pressure, and humidity of the semi-enclosed area space, wherein the input parameters are adjusted under computer control to the input parameters to preserve the 0.5-0.9 μm particle size while maintaining the applied air pressure at the nozzle outlet within 5-25 psi.

17. The system of claim 14, wherein the set fluid properties of the cleaning fluid comprise applied air pressure at the nozzle outlet and fluid flow rate, wherein reducing applied air pressure at the nozzle outlet below 25 psi is accompanied by reducing flow to maintain 0.5-0.9 μm particles.

* * * * *